(12) United States Patent
Asolkar et al.

(10) Patent No.: US 9,259,446 B2
(45) Date of Patent: Feb. 16, 2016

(54) CHEMICAL AND BIOLOGICAL AGENTS FOR THE CONTROL OF MOLLUSCS

(71) Applicant: Marrone Bio Innovations, Inc., Davis, CA (US)

(72) Inventors: Ratnakar Asolkar, Davis, CA (US); Sarahann Rackl, Austin, TX (US); Huazhang Huang, Durham, NC (US); Marja Koivunen, Davis, CA (US); Pamela Marrone, Davis, CA (US)

(73) Assignee: MARRONE BIO INNOVATIONS, INC., Davis, CA (US)

( * ) Notice: Subject to any disclaimer, the term of this patent is extended or adjusted under 35 U.S.C. 154(b) by 0 days.

(21) Appl. No.: 14/604,514

(22) Filed: Jan. 23, 2015

(65) Prior Publication Data

US 2016/0015032 A1    Jan. 21, 2016

Related U.S. Application Data

(63) Continuation of application No. 13/716,483, filed on Dec. 17, 2012, now Pat. No. 8,968,723, which is a continuation of application No. 12/763,892, filed on Apr. 20, 2010, now abandoned.

(60) Provisional application No. 61/170,686, filed on Apr. 20, 2009, provisional application No. 61/170,790, filed on Apr. 20, 2009, provisional application No. 61/285,525, filed on Dec. 10, 2009.

(51) Int. Cl.
*A61K 36/00* (2006.01)
*A61K 35/618* (2015.01)

(52) U.S. Cl.
CPC .................................. *A61K 35/618* (2013.01)

(58) Field of Classification Search
None
See application file for complete search history.

(56) References Cited

U.S. PATENT DOCUMENTS

| | | | |
|---|---|---|---|
| 4,542,097 | A | 9/1985 | Labows, Jr. et al. |
| 4,560,656 | A | 12/1985 | Farbood et al. |
| 5,527,525 | A | 6/1996 | Wilson et al. |
| 6,194,194 | B1 | 2/2001 | Molloy |
| 6,451,565 | B1 | 9/2002 | Rabenhorst et al. |
| 7,129,067 | B2 | 10/2006 | Mitsuhashi et al. |
| 2004/0234629 | A1 | 11/2004 | Nakazato et al. |
| 2010/0266717 | A1 | 10/2010 | Asolkar et al. |
| 2011/0021358 | A1 | 1/2011 | Huang et al. |
| 2012/0121745 | A1 | 5/2012 | Rackl et al. |
| 2013/0121978 | A1 | 5/2013 | Asolkar et al. |
| 2013/0196013 | A1 | 8/2013 | Asolkar et al. |

FOREIGN PATENT DOCUMENTS

| | | |
|---|---|---|
| GB | 1409321 A | 10/1975 |
| KR | 10-0130075 B1 | 4/1998 |
| WO | WO 91/00012 | 1/1991 |
| WO | WO 93/00816 | 1/1993 |
| WO | WO 94/08904 | 4/1994 |
| WO | WO 2007/031565 | 3/2007 |
| WO | WO/2008/012756 | 1/2008 |
| WO | WO/2008/665451 | 6/2008 |
| WO | WO 2008/130558 | 10/2008 |
| WO | WO 2013/130680 | 9/2013 |

OTHER PUBLICATIONS

Abouseoud, M., "Biosurfactant Production from Olive Oil from *Pseudomonas fluorescens*," *Communicating Current Research and Educational Topics and Trends in Applied Microbiology* p. 340-347 (2007).

Abouseoud, M. et al., "Evaluation of Different Carbon and Nitrogen Sources in Production of Biosurfactant by *Pseeudomonas fluorescens*," *Desalination* 223:143-151 (2008).

Aguedo, M. et al., "Mechanisms Underlying the Toxicity of Lactone Aroma Compounds Towards the Producing Yeast Cells," *Journal of Applied Microbiology* 94:258-265 (2003).

Alchihab et al., "Production of γ-Decalactone by a Psychrophilic and a Mesophilic Strain of the Yeast *Rhodotorula aurantiaca*, *Appl Biochem Biotechnol.*" 158: 41-50. 2009.

Andersson, R.E. et al., "Lipase Production, Lipolysis, and Formation of Volatile Compounds by *Pseudomonas fluorescens* in Fat Containing Media," *Journal of Food Science* 45:1694-1701 (1980).

Asolkar, R., et al. "Daryamides A-C, weakly cytotoxic polyketides from a marine-derived actinomycete of the genus *Streptomyces* strain CNO-085." J. Nat. Prod. 69: 1756-1759. 2006.

Bangera, G.M. et al., "Identification and Characterization of a Gene Cluster for Synthesis of the Polyketide Antibiotic 2,4-Diacetylphloroglucinol from *Pseudomonas fluorescens* Q2-87," *Journal of Bacteriology* 181(10):3155-3163 (1999).

Barrasa, J.L.M. et al., "Antibacterial Susceptibility Patterns of *Pseudonomas* Strains Isolated from Chronic Canine Otitis Externa," *Journal of Vetirenary Medicine* B 47: 191-196 (2000).

Baum, M.M. et al., "Characterization of Structures in Biofilms Formed by a *Pseudomonas fluorescens* Isolated From Soil," *BMC Microbiology* 9:103 (2009).

Bejarano, A. et al., "Bioavailability of the Organophosphorous Insecticide Chlorpyrifos to the Suspension-Feeding Bivalve, Mercenaria Mercenaria, following Exposure to Dissolved and Particulate Matter." *Environmental Toxicology and Chemistry*, vol. 22, No. 9. (2003).

Blumer, C. et al., "Global GacA-Steered Control of Cyanide and Exoprotease Production in *Pseudomonas fluorescens* Involves Specific Ribosome Binding Sites," *PNAS* 96(24):14073-14078 (1999).

(Continued)

*Primary Examiner* — Qiuwen Mi
(74) *Attorney, Agent, or Firm* — Ying-Horng Liu; Chainey P. Singleton; Marrone Bio Innovations

(57) ABSTRACT

Compositions and methods for controlling molluscs, members of the Gastropoda and Bivalvia classes which includes but is not limited to lactones, lactams, carbamates, amides, and/or carboxylic acid containing compounds as active ingredients and/or compounds derived from *Pseudomonas* and/or *Erwinia*. Also provided are methods and compositions for increasing the efficacy of chemical and biological control for invasive molluscs in open waters, power plants, and drinking water treatment facilities under coldwater conditions.

8 Claims, 5 Drawing Sheets

(56) References Cited

OTHER PUBLICATIONS

Brader, G. et al. "Altering Substrate Chain Length Specificity of an Acylhomoserine Lactone Synthase in Bacterial Communication," *J. Biol. Chem.* 280:10403-10409 (2005).
Burgess, J.G. et al., "The Development of a Marine Natural Product-Based Antifouling Paint," Biofouling 19(Supplement):197-205 (2003).
Chalier, P. et al., "Enantiodifferentiation of Four γ-Lactones Produced by *Penicillium Roqueforti*," *Chirality* 10:786-790 (1998).
Chapalain, A. et al., "Comparative Study of 7 Fluorescent Pseudomonad Clinical Isolates," *Canadian Journal of Microbiology* 54:19-27 (2008).
Choi, H.J. et al., "Involvement of Epidermal Growth Factor Receptor-Linked Signaling Responses in Pseudomonas fluorescens-Infected Alveolar Epithelial Cells," *Infection and Immunity* 79(5):1998-2005 (2011).
Connelly, N. et al. "Economic Impacts of Zebra Mussels on Drinking Water Treatment and Electric Power Generation Facilities." Environ. Manage 40: 105-112. (2007).
Darrigan, G. et al., "The Golden Mussel, Limnoperna Fortunei (Dunker, 1857) (Bivalvia: Mytilidae), in the Neotropical Region: A 10 Year Story of Invasion," Tentacle No. 11:8-9 (2003).
De Villiers et al., "Structure and Activity in Molluscides". Nature, Mar. 1967.
Dietz, T.H. et al., "Osmotic and Ionic Regulation of North American Zebra Mussels (*Dreissena polymorpha*)," *American Zoologist* 36:364-372 (1996).
Domenech, C.E. et al., "*Pseudomonas aeruginosa* Cholinesterase and Phosphorylcholine Phosphatase: Two Enzymes Contributing to Corneal Infection," *FEMS Microbiology Letters* 82:131-136 (1991).
Dufosse, L. et al., "Chirality of the γlactones produced by *Sporidiobolus salmonicolor* grown in two different media." Chirality 9: 667-671. (1997).
El-Sayed, K.A. et al., "Characterization of the Mupirocin Biosynthesis Gene Cluster from *Pseudomonas fluroescens* NCIMB 10586," *Chemistry & Biology* 10:419-430 (2003).
Flodgaard, L.R. et al., "Nonbioluminescent Strains of *Photobacterium Phosphoreum* Produce the Cell-to-Cell Communication Signal N-(3-Hydroxyoctanoyl)homoserine Lactone," *Applied and Environmental Microbiology* 71:2113-2120 (2005).
Furukawa, H. et al., "Ferulic Acid Production from Clove Oil by *Pseudomonas fluorescens* E188," *Journal of Bioscience and Bioengineering* 96(4):404-405 (2003).
Gershman, M.D. et al., "Multistate Outbreak of *Pseudomonas fluorescens* Bloodstream Infection after Exposure to Contaminated Heparinized Saline Flush Prepared by a Compounding Pharmacy," *Clinical Infectious Diseases* 47:1372-1379 (2008).
Gibb, A.P. et al., "Rate of Growth of *Pseudomonas fluorescens* in Donated Blood," *Journal of Clincal Pharmacology* 48:717-718 (1995).
Gimmestad, M. et al., "The *Pseudomonas fluorescens* AlgG Protein, but Not Its Mannuronan C-5-Epimerase Activity, is Needed for Alginate Polymer Formation," *Journal of Bacteriology* 185(12):3515-3523 (2003).
Gocho, S. et al. "Biotransformation of oleic acid to optically active γ-dodecalactone." Biosci. Biotech. Biochem. 59: 1571-1572. (1995).
Ekelund, R. et al., "Influence of Suspended Solids on Bioavailabilit y of Hexachlorobenzene and Lindane to the Deposit-Feeding Marine Bivalve, Abra nitida (Muller)" Bulletin of Envionmental Contamination and Toxicology, vol. 38, No. 3, (1987).
Hinsa, S.M. et al., "Biofilm Formation by *Pseudomonas fluorescens* WCS365: A Role for LapD," *Microbiology* 152:1375-1383 (2006).
Howell, C.R. et al., "Suppression of Pythium ultimum-Induced Damping-Off of Cotton Seedlings by *Pseudomonas fluorescens* and its Antibiotic, Pyoluteorin," *Phytopathology* 70(8):712-715 (1980).
Hsueh, P. et al., "Outbreak of *Pseudomonas fluorescens* Bacteremia Among Oncology Patients," *Journal of Clinical Microbiology* 36:(10):2914-2917 (1998).

Itoh, Y. et al., "A Novel Hepatoprotective γ-Lactone, MH-031. I. Disclovery, Isolation, Physico-Chemical Properties and Structural Elucidation," *J. Antibiotics* 44:832-837 (1991).
Ishihara, K. et al., "Effective Production of *Pseudomonas fluorescens* Lipase by Semi-Batch Culture with Turbidity-Dependent Automatic Feeding of Both Olive Oil and Iron Ion," *Applied Microbiology and Biotechnology* 31:45-48 (1989).
Jackson, M.K. et al., "Necrotizing Hepatitis in Pet Birds Associated with *Pseudomonas fluorescens*," *Avian Diseases* 40:473-476 (1996).
Jiang, Y. et al., "High Poly(β-hydroxybutyrate) Production by *Pseudomonas fluorescens* A2a5 from Inexpensive Substrates," *Enzyme and Microbial Technology* 42:167-172 (2008).
Karatayev, A.Y. et al., "The Effects of *Dreissena Polymorpha* (Pallas) Invasion on Aquatic Communities in Eastern Europe," *J. Shellfish Research* 16:187-203 (1997.
Kisaalita, W.S. et al., "Defined Media for Optimal Pyoverdine Production by *Pseudomonas fluorescens* 2-79," *Applied Microbiology and Biotechnology* 39:750-755 (1993).
Kojima, Y. et al., "Purification and Characterization of an Alkaline Lipase from *Pseudomonas fluorescens* AK102," *Biosci. Biotech. Biochem.* 58(9):1564-1568 (1994).
Koka, R. et al., "Isolation and Characterization of a Protease from *Pseudomonas fluorescens* RO98," *Journal of Applied Microbiology* 89:280-288 (2000).
Kramer, K.J.M. et al., "The 'Musselmonitor®' as Biological Early Warning System, The First Decade," in *Biomonitors and Biomarkers as Indicators of Environmental Change 2, Environmental Science Research* 56:59-87 (2000).
Liao, C. et al., "Biochemical and Genetic Characterization of an Extracellular Protease from *Pseudomonas fluorescens* CY091," *Applied and Environmental Microbiology* 64(3):914-921 (1998).
Lorenzo, M. et al., "$^{13}$C NMR-Based Empirical Rules to Determine the Configuration of Fatty Acid Butanolids. Novel γ-Dilactones from *Pterogorgia* spp," *Organic Letters* 8:5001-5004 (2006).
Mackie, G.L. et al., "Comparative Biology of Zebra Mussels in Europe and North America: An Overview," *American Zoologist* 36:244-258 (1996).
Madi, A. et al., "The Clinical *Pseudomonas fluorescens* MFN1032 Strain Exerts a Cytotoxic Effect on Epithelial Intestinal Cells and Induces Interleukin-8 via the AP-1 Signaling Pathway," *BMC Microbiology* 10:215 (2010).
Macisaac, H.J., "Potential Abiotic and Biotic Impacts of Zebra Mussels on the Inland Waters of North America," *Amer. Zool.* 36:287-299 (1996).
Madi, A. et al., "*Pseudomonas fluorescens* Alters Epithelial Permeability and Translocates Across Caco-2/TC7 Intestinal Cells," *Gut Pathogens* 2:16 (2010).
Manfredi, R. et al., "*Pseudomonas* Organisms Other than *Pseudomonas Aeruginosa* as Emerging Bacterial Pathogens in Patients with Human Immunodeficiency Virus Infection," *Infectious Diseases in Clinical Practice* 9:79-87 (2000).
McMahon, R.F., "The Physiological Ecology of the Zebra Mussel, *Dreissena polymorpha*, in North America and Europe," *American Zoologist* 36:339-363 (1996).
Miller, S.L. et al., "Axinellamide, a New Alkaloid from the Marine Sponge *Axinella* Sp.," *Tetrahedron Letters* 36:5851-5852 (1995).
Mills, E.L. et al., "A Review of the Biology and Ecology of Quagga Mussel (*Dreissena bugensis*), a Second Species of Freshwater Dreissenid Introduced to North America," *American Zoologist* 36:271-286 (1996).
Mizobuchi, S. et al., "Antifouling Substances Against the Mussel in an Octocoral *Dendronephthya* sp.," *Nippon Suisan Gakkaishi* 59(7):1195-1199 (1993).
Molloy, D.P., "The Potential for Using Biological Control Technologies in the Management of *Dreissena* Spp.," *J. Shellfish Res.* 17:177-183 (1998).
Molloy, D.P. et al., "Overview of a Novel Green Technology: Biological Control of Zebra and Quagga Mussels with *Pseudomonas fluorescens*," Bacterial Project Overview 6:1-9 (2007).
Molloy, D.P., "Environmentally Safe Control of Zebra Mussel Fouling," Technical Report (R41909R09) retrieved from the internet at

(56) References Cited

OTHER PUBLICATIONS http://www.netl.doe.gov/technologies/coalpower/ewr/pubs/NT41909_NY%20Dept%20of%20Educ_Final%20Report.pdf (May 21, 2008).
Molloy, D.P. et al., "Mode of Action of *Pseudomas fluorescens* Strain CL145A, a Lethal Control Agent of Dreissenid Mussels (Bivalvia: Dreissenidae)," *J. Invertebrate Pathology* 113:115-121 (2013).
Murty, M.G. et al., "Production of a Mosquitocidal Exotoxin by a *Pseudomonas fluorescens* Strain," *Journal of Invertebrate Pathology* 64:68-70 (1994).
Nowak-Thompson, B. et al., "Characterization of the Pyoluteorin Biosynthetic Gene Cluster of *Pseudomonas fluorescens* Pf-5," *Journal of Bacteriology* 181(7):2166-2174 (1999).
Oliveira, M.D. et al., "Forecasting the Expansion of the Invasive Golden Mussel Llmnoperna fortune in Brazilian and North American Rivers Based on its Occurrence in the Paraguay River and Pantanal Wetland of Brazil," *Aquatic Invasions* 5:59-73 (2010).
O'Neill, C.R., Jr. "Economic impact of zebra mussels-results of the 1995 national zebra mussel information clearing house study." Gt. Lakes Res. Rev. 3: 35-44. 1997.
Parente, A.M. et al., "Ultrastructural Aspects of Autolysis of *Pseudomonas fluorescens* Induced by Osmotic Shock," *Journal of General Microbiology* 130:1459-1470 (1984).
Peighami-Ashnaei, S. et al., "Interaction of Different Media on Production and Biocontrol Efficacy of *Pseudomonas fluorescens* P-35 and *Bacillus subtilis* B-3 Against Grey Mold of Apple," *Journal of Plant Pathology* 91(1):65-70 (2009).
Perry, K. et al., "Detecting Physiological and Pesticide-Induced Apoptosis in Early Developmental Stages of Invasive Bivalves," *Hydrobiologia* 628:153-164 (2009).
Peyer, S.M. et al., "Zebra Mussels Anchor Byssal Threads Faster and Tighter than Quagga Mussels in Flow," *The Journal of Experimental Biology* 212:2027-2036 (2009).
Picot, L. et al., "*Pseudomonas fluorescens* as a Potential Pathogen: Adherence to Nerve Cells," *Microbes and Infection* 3:985-995 (2001).
Prabakaran, G. et al., "Isolation of a *Pseudomonas fluorescens* Metabolite/Exotoxin Active Against Both Larvae and Pupae of Vector Mosquitoes," *Pest Management Science* 59:21-24 (2002).
Prabakaran, G. et al., "Development of Cost-Effective Medium of the Large-Scale Production of a Mosquito Pupicidal Metabolite from *Pseudomonas fluorescens* Migula," *Biological Control* 48:264-266 (2009).
Rajmohan, S. et al., "Enzyme from Isolates of *Pseudomonas fluorescens* Involved in Food Spoilage," *Journal of Applied Microbiology* 93:205-213 (2002).
Ramette, A. et al., "*Pseudomas protegens* sp. nov., Widespread Plant-Protecting Bacteria Producing the Biocontrol Compounds 2,4-Diacetylphloroglucinol and Pyoluteorin," *Systematic and Applied Microbiology* 34:180-188 (2011).
Ravi, B. et al., "Lipid and Terpenoid Metabolites of the Gorgonian *Plexaura flava*," Aust. J. Chem. 35: 105-12. 1982.
Rezanka, T. et al., "γ-Lactones from the Soft Corals *Sarcophyton trocheliophorum* and *Lithophyton arboreum*," *Tetrahedron* 57:8743-8749 (2001).
Ricciardi, A., "Global Range Expansion of the Asian Mussel *Limnoperna Fortunei* (Mytilidae): Another Fouling Threat to Freshwater Systems," *Biofouling* 13(2):97-106 (1998).
Rochu, D. et al., "Purification, Molecular Characterization and Catalytic Properties of *Pseudomonas fluorescens* Enzyme Having Cholinesterase-Like Activity," *Biochemica et Biophysica Acta* 1385:126-138 (1998).
Rossignol, G. et al., "Involvement of a Phospholipase C in the Hemolytic Activity of a Clinical Strain of *Pseudomonas fluorescens*," *BMC Microbiology* 8:189 (2008).
Rodriguez, A., et al., "Further butenolides from the Caribbean octocoral *Pterogorgia citrine*." Journal of Natural Products. 57: 339-347. 1994.
Rossignol, G. et al., "Phenotypic Variation in the *Pseudomonas fluorescens* Clinical Strain MFN 1032," *Research in Microbiology* 160:337-344 (2009).
Sakuda, S. et al., "Biosynthetic Studies on Virginiae Butanolide A, a Butyrolactone Autoregulator from *Streptomyces*. Part 2, Preparation of Possible Biosynthetic Intermediates and Conversion Experiments in a Cell-free System." J. Chem. Soc. Perkin Trans. I 2309-2315. 1993.
Seo, S-T et al., "Characterization of an Antibacterial Substance Produced by *Erwinia carotovora* subsp. carotovora Ecc 32," *J. Gen. Plant Pathol.* 70:273-277 (2004).
Sandler, J.S. et al., "Cytotoxic β-Carbolines and Cyclic Peroxides from the Palauan Sponge *Plakortis nigra*," *J. Nat. Prod.* 65:1258-1261 (2002).
Shaaban, K.A. et al., "Electrospray Ionization Mass Spectra of Piperazimycins A and B and γ-Butyrolactones from a Marine-Derived *Streptomyces* sp.," *J. Antibiot.* 61:736-746 (2008).
Shao, Y.Y. et al., "Chemical constituents of *Antrodia camphorata* submerged whole broth." Nat. Prod. Res. 22: 1151-1157. 2008.
Silby, M.W. et al., "*Pseudomonas* Genomes: Diverse and Adaptable," *FEMS Microbiology Reviews* 35:652-680 (2011).
Silverman, H. et al., "Gill Structure in Zebra Mussels: Bacterial-Sized Particle Filtration," *American Zoologist* 36:373-384 (1996).
Sugiura, M. et al., "Purification, Crystallization and Properties of Triacylglycerol Lipase from *Pseudomonas fluorescens*," *Biochimica et Biophysica Acta* 488:353-358 (1977).
Tan, K.H. et al., "Effect of Culture Conditions on Batch Growth of *Pseudomonas fluorescens* on Olive Oil," *Applied Microbiology and Biotechnology* 23:27-32 (1985).
Tan, K.H. et al., "Utilization of Substrates During Batch Growth of *Pseudomonas fluorescens* on Olive Oil, Lard, and Mutton Tallow," *Applied Microbiology and Biotechnology* 26:443-446 (1987).
Thomashow, L.S. et al., "Role of a Phenazine Antibiotic from *Pseudomonas fluorescens* in Biological Control of *Gaeumannomyces graminis var. tritici*," *Journal of Bacteriology* 170(8):3499-3508 (1988).
Veron, W. et al., "Natriuretic Peptides Modify *Pseudomonas fluorescens* Cytotoxicity by Regulating Cyclic Nucleotides and Modifying LPS Structure," *BMC Microbiology* 8:114 (2008).
Von Graevenitz, A. et al., "Pathogenic Significance of *Pseudomonas Fluorescens* and *Pseudomonas Putida*," *Yale Journal of Biology and Medicine* 44:265-273 (1971).
Wang, S. et al., "Production of Antifungal Materials by Bioconversion of Shellfish Chitin Wastes Fermented by *Pseudomonas fluorescens* K-188," *Enzyme and Microbial Technology* 36:49-56 (2005).
Shen, Y-C. et al., "Novel Linear C22-Sesterterpenoids from Sponge Ircinia formosana," Tetrahedron Letters 47:4007-4010 (2006).
Takougang, I. et al., "Field Trials of Low Dose Bayluscide on Snail Hosts of Schistosome and Selected Non-Target Organisms in Sahelian Cameroon," Mem. Inst. Oswaldo Cruz 101(4):355-358 (2006).
U.S. Army Corps of Engineers Waterways Experiment Station, "Zebra Mussels: Biology, Ecology, and Recommended Control Strategies," Zebra Mussel Research Technical Note ZMR-1-01, Zebra Mussel Research Program, 9 pages (1995).
U.S. Geological Survey, Florida Caribbean Science Center, "Nonindigenous Species Information Bulletin: Asian Clam, Corbicula fluminea," No. 2001-001 (2001).
Vieira, P.C. et al., "γ-Lactones from Iryanthera Species," Phytochemistry 22:711-713 (1983).
Wei, B. et al., "Pseudomonas fluorescens Encodes the Crohn's Disease-Associated I2 Sequence and T-Cell Superantigen," Infection and Immunity 70(12):6567-6575 (2002).
Winson, M.K. et al., "Multiple N-acyl-L-Homoserine Lactone Signal Molecules Regulate Production of Virulence Determinants and Secondary Metabolites in Pseudomonas aeruginosa," PNAS 92:9427-9431 (1995).

CHEMICAL AND BIOLOGICAL AGENTS FOR THE CONTROL OF MOLLUSCS

PRIORITY CLAIM

This application is a continuation under 35 U.S.C. §120 of application Ser. No. 13/716,483, filed Dec. 17, 2012. Ser. No. 13/716,483 is a continuation under 35 U.S.C. §120 of application Ser. No. 12/763,892, filed Apr. 20, 2010, the contents of which are incorporated herein by reference. Ser. No. 12/763,892 also claims priority under 35 USC §119(e) from U.S. application Ser. No. 61/170,790, filed Apr. 20, 2009, U.S. application Ser. No. 61/170,686, filed Mar. 16, 2009 and U.S. application Ser. No. 61/285,525, filed Dec. 10, 2010, the contents of which are incorporated herein by reference.

FIELD OF THE INVENTION

Compositions and methods for controlling molluscs, such as mussels and/or snails and/or slugs which includes but is not limited to lactones, lactams, carbamates, amides, and/or carboxylic acid containing compounds as active ingredients and/or compounds derived from a microbe (e.g., *Pseudomonas* and/or *Erwinia*). Also provided are methods and compositions for increasing the efficacy of chemical and biological control for molluscs, such as mussels and/or snails and/or slugs in open waters, power plants, and drinking water treatment facilities under coldwater conditions or solid surfaces.

BACKGROUND OF THE INVENTION

The Zebra mussel, *Dreissena polymorpha*, was originally native to the Caspian Sea and the Ural River in Asia. In the nineteenth century, it spread west and now occurs in most of Europe, the western portion of the Commonwealth of Independent States (formally the Soviet Union), and Turkey. Over two decades ago, the mussels, such as zebra mussel, *Dreissena polymorpha* and quagga mussel, *Dreissena bugensis*, were introduced into North America. Their wide spread through inland waters has led to the coverage of most of eastern of US [U.S. Army Engineer Waterways Experiment Station. 1995. Zebra mussels: Biology, Ecology, and Recommended Control Strategies. Technical Note. ZMR-1-01. Zebra Mussel Research Program, Vicksburg, Miss.]. Similarly, Golden Mussel, *Limnoperna fortune*, affected Asian and Southern American countries (Golden Mussel—*Limnoperna fortune*). Asian Clam *Corbicula fluminea* almost spread all Asian countries and US [Non-indigenous species information bulletin: Asian clam, *Corbicula fluminea* (Müller, 1774) (Mollusca: Corbiculidae)]. And other mussels such unionid mussels exist in US and other countries.

The ability of the mussels to quickly colonize new areas, rapidly achieve high densities and attach to any hard substratum (e.g., rocks, logs, aquatic plants, shells of native mussels, and exoskeletons of crayfish, plastic, concrete, wood, fiberglass, pipes made of iron and polyvinyl chloride and surfaces covered with conventional paints) make them to cause serious adverse consequences. These consequences include damages of water-dependent infrastructure, increased millions of dollars in the operating expense and significant damage of the ecological systems [O'Neill, C. R., Jr. 1997, Economic impact of zebra mussels-results of the 1995 national zebra mussel information clearing house study. *Gt. Lakes Res. Rev.* 3, 35-44; Karatayev, A. Y., L. E. Burlakova, D. K., Padilla, 1997, the effects of *Dreissena polymorpha* (Pallas) invasion on aquatic communalities in eastern Europe. *Journal Shellfish Research*, 16, 187-203; MacIsaac, H. J., 1996. Potential abiotic and biotic impacts of zebra mussels on the inland waters of North America. *American Zoology*, 36, 289-299; D. P. Molloy, the potential for using biological control technologies in the management of *Dreissena* SPP, *Journal of Shellfish Research*, 1998 (17) 177-183] as well as productivity reduction which costs billions of dollars in lost revenue (Connelly, N. A., C. R. O'Neill, Jr, et al. (2007), "Economic impacts of Zebra mussels on drinking water treatment and electric power generation facilities", Environmental Management 90:10. Economic impacts of zebra mussels on drinking water treatment and electric power generation facilities. Environmental Management 40: 105-112). Additionally, rapid invasion of aquatic ecosystems by these invasive mussels has caused decline in the richness and abundance of endemic unionid mussels, an important part of biodiversity (Ricciardi, A, Neves, R. J., Rasmussen, J. B. 1998. Impending extinctions of North American freshwater mussels (Unionidae) following the zebra mussel (*Dreissena polymorpha*) invasion. Journal of Animal Ecology 67: 613-619).

Management of mussels is very important for protecting water-dependent infrastructure and water ecological systems. There are many ways to reduce the populations of mussels. These methods include pre-active and reactive methods. Reactive removal includes the mechanical removal, predator removal, and chemical and biochemical removal. For example, fish, birds, crayfish, crabs, leeches and mammals have shown to predate mussels. However, it is unlikely that mussel population will be controlled by natural predation, especially in man-made structures such as pipes or pumping plants.

Application of molluscicides is another effective ways to reduce the mussel population. For example, sodium hypochlorite is a commonly used control agent in Europe, US, and Canada. However, mussels can withstand this treatment for several days by closing their shells and chlorine can be only used in pipes or ducts that contain pressure sensing or other equipment due to environmental toxicity of chlorine [U.S. Army Engineer Waterways Experiment Station. 1995. Zebra mussels: Biology, Ecology, and Recommended Control Strategies. Technical Note. ZMR-1-01. Zebra Mussel Research Program, Vicksburg, Miss.]. In addition, there are many other commercialized molluscicides such as surfactant ammonium salts, Butylated hydroxytoluene (BHT) in paints, N-triphenylmethyl-morpholine and so on. These chemicals either low selectivity or affect the water ecosystems. For example, a 4-trifluroethyl-4-nitrophenol marketed as Bayluscide® (Bayer) is a possible candidate for control such invasive exotic species. However, the toxic mechanism of such a chemical is to affect mussel cellular respiration, which in nature will limit its selectivity between mussel and other aquatic species such as fish [Karen Perry Æ John Lynn, Detecting physiological and pesticide-induced apoptosis in early developmental stages of invasive bivalves, Hydrobiologia (2009) 628:153-164; I Takougang, J Meli, F Angwafo, Field trials of low dose Bayluscide on snail hosts of schistosome and selected non-target organisms in sahelian Cameroon, Mem Inst Oswaldo Cruz, Rio de Janeiro, 2006, 101(4): 355-358].

It is crucial to manage the invasive mussels in a safe, environmental friendly and cheap manner. In order to find less harmful methods to control these invasive mussels, New York State Museum's (NYSM) Field Research Laboratory screened more than 700 bacterial isolates as potential biological control agents to be used against zebra and *quagga* mussels. As a result, they found an isolate, strain CL145A of *Pseudomonas fluorescens*, to be lethal to these mussels (see Molloy, D. P. U.S. Pat. No. 6,194,194, issued Feb. 27, 2001).

This bacterium is worldwide in distribution and is present in all North American waterbodies. In nature it is a harmless bacterial species that is found protecting the roots of plants from rot and mildew. It is so ubiquitous that it is a common food spoilage organism in the average household refrigerator [Daniel P. Molloy and Denise A. Mayer, Overview of a Novel Green Technology: Biological Control of Zebra and *Quagga* Mussels with *Pseudomonas fluorescens*, Version 6: Updated Aug. 24, 2007].

Lactones, Lactams, Carbamate and Amides

Lactones are widely distributed in foods and beverages, and are also secondary metabolites of animals (e.g., sponges) and microorganisms (e.g., yeasts, fungi). Some lactones have a special aroma (e.g., gamma-decalactone), resulting in an increasing demand for natural products in food industry by the use of biotechnological processes for the production of these lactones [Mohamed Alchihab, Jacqueline Destain, Mario Aguedo, Lamia Majad, Hakim Ghalfi, Jean-Paul Wathelet, Philippe Thonart, Production of γ-Decalactone by a Psychrophilic and a Mesophilic Strain of the Yeast *Rhodotorula aurantiaca*, Appl Biochem Biotechnol (2009) 158:41-50]. Other functions of different lactones are associated with antibacterial activity [Ikuko Shimizu, Yasunori Isshiki, Harue Nomura, Keisuke Sakuda, Katsuya Sakuma, Seiichi Kondo, The Antibacterial Activity of Fragrance Ingredients against *Legionella pneumophila*, Biol. Pharm. Bull. 2009, 32(6) 1114-1117], hepatoprotective activity [Yumiko Itoh, Hiroshi Shimura, Mayumi Ito, Naoharu Watanabe, Michio Yamagishi, Masaharu Tamai and Kazunori Hanada, Novel hepatoprotective γ-lactone, MH-031, I. Discovery isolation, physicochemical properties and structural elucidation, The Journal of Antibiotics 1991, 832-837], anti-tuberculosis activity [Ma, G. Y. et al. anti-tuberculosis constituents from the stem bark of *micromelum hirsutum*, Planta Med. 2005, 71, 261-267], anti-HIV activity [zhang et al., sesquiterpenes and butenolides, natural anti-HIV constituents from *Litse verticillate*, Planta Med, 2005, 71, 452-457], sex pheromone [J. H. Tumlinson, Identification of the Female Japanese Beetle Sex Pheromone Inhibition of Male Response by an Enantiomer, Science, 1977, 197, 789-792], cytotoxic activity [Fan, X. N. et al. Chemical Constituents of *Heteroplexis micocephala*, J. Nat. Prod. 2009, 72, 1184-1190], signal molecules [M. K. Vinson, et al. Multiple N-acyl-L-homoserine lactone signal molecules regulate production of virulence determinants and secondary metabolites in *Pseudomonas aeruginosa*, Proc. Natl. Acad. Sci. USA, 1995, 92, 9427-9431] and insecticidal activity [John A. Findlay, et al., Insect toxins from spruce endophytes, Can. J. Chem. 2003, 81, 284-292], Although lactams exist in some plants and marine organisms, they often are fungal metabolites. Many biological activities (e.g., cytotoxic and antitumor activity, angiogenesis inhibition, neuronal activity, anti-infectious activities) were reviewed in a recent publication [Bastien Nay, Nassima Riache and Laurent Evanno, Chemistry and biology of non-tetramic γ-hydroxy-γ-lactams and γ-alkylidene-γ-lactams from natural sources, Natural Product reports, 2009, 26, 1044-1062].

Carbamates exist in plants, microorganism and sponges, but fewer biological activities are reported for these compounds in comparison with lactones, amides because many of these compounds are not stable in aqueous solutions. There was one example of fungicidal activity of natural carbamates [Richard J. Clark, et al., Antifungal Alkyl Amino Alcohols from the Tropical Marine Sponge *Haliclona* n. sp., J. Nat. Prod. 2001, 64, 1568-1571].]. Amides are widely distributed in plants, microorganisms and sponges. For example, Scalusamide A from marine-derived fungus *Penicillium citrinum* exhibited antibacterial and antifungal activity [Masashi Tsuda, et al., Scalusamides A-C, New Pyrrolidine Alkaloids from the Marine-Derived Fungus *Penicillium citrinum*, J. Nat. Prod. 2005, 68, 273-276].

Another example of an amide is a plant-derived compound called sarmentine, which displayed a lot of bioactivities. As described in application Ser. No. 61/227,412, Jul. 21, 2009 sarmentine was first isolated from the fruit of *Piper sarmentosum* in 1987 [Likhitwitayawuid, K., Ruangrungsi, N, Lange, G and Decicco, C., Structural Elucidation and Synthesis of New Components isolated from *Piper Samentosum*, Tetrahedron 1987 (43) 3689-3694] and also from *Piper nigrum* in 1988 [Kiuchi, F., Nakamura, N., Tsuda, Y., Kondo, K and Yoshimura, H. Studies on Crude Drugs Effective on Visceral Larva Migrans. IV. Isolation and Identification of Larvicidal Principles in Pepper Chemical and Pharmaceutical Bulletin 1988(36):2452], and first synthesized in 1995 [Bernabeu, M., Chinchilla, R. and Najera, C., (2E,4E)-5-Tosyl-2,4-pentadienamides: New Dienic Sulfones for the Stereoselective Synthesis of (2E,4E)-Dienamides, Tetrahedron Letter, 1995 (36)3901-3904]. Sarmentine has been found to act as an in vivo skin antioxidant protecting photo-aged skin [Cornacchione, S.; Sadick, N. S.; Neveu, M.; Talbourdet, S.; Lazou, K.; Viron, C.; Renimel, I.; de Quéral, D.; Kurfurst, R.; Schnebert, S.; Heusèle, C.; André, P.; Perrier E. In vivo skin antioxidant effect of a new combination based on a specific *Vitis vinifera* shoots extract and a biotechnological extract. J. Drugs in Dermatol. 2007, 6S, 8-13], display antiplatelet aggregation activity [Li, C. Y.; Tsai, W.; Damu, A. G.; Lee, E. J.; Wu, T. S.; Dung. N. X.; Thang, T. D.; Thanh, L. Isolation and identification of antiplatelet aggregatory principles from the leaves of *Piper lolot*, J. Agric. Food Chem. 2007, 55, 9436-9442], have antiplasmodial and antimycobacterial activities [Tuntiwachwuttikul, P.; Phansa, P.; Pootaengon, Y.; Taylor, W. C. Chemical constituents of the roots of *Piper Sarmentosum*, Chem. Pharm. Bull. 2006, 54, 149-151] and antituberculosis activity [Rukachaisirikul, T.; Siriwattanakit, P.; Sukcharoenphol, K.; Wongvein, C.; Ruttanaweang, P.; Wongwattanavuch, P.; Suksamrarn, A. Chemical constituents and bioactivity of *Piper sarmentosum*, J. Ethnopharmacol., 2004, 93, 173-176]. Sarmentine is used as a solubilizer of hydrophobic compounds in cosmetics and pharmaceuticals (Stephen, T.; Andrew, H. Compositions comprising macromolecular assembles of lipid surfactant, PCT Publication No. WO/2008/065451). Application Ser. No. 61/227,412, Jul. 21, 2009 further discloses that sarmentine and its analogs may be used to control plant pests.

BRIEF SUMMARY OF THE INVENTION

This invention is directed to the compounds, compositions and methods for controlling molluscs, particularly members of the Gastropoda and/or Bivalvia classes and more particularly mussels, snails and slugs. The invention is directed to isolated compounds obtainable or derived from (a) microorganism, particularly, *Pseudomonas* species, more particularly, *Pseudomonas fluorescens* or alternatively, an organism having the identifying characteristics of *Pseudomonas* ATCC 55799; (b) is toxic to a member of a class of molluscs selected from the group consisting of Bivalvia, particularly, mussels (e.g., *Dreissana* sp.) and/or Gastropoda, particularly, snails, which includes but is not limited to aquatic snails (e.g., *Biomphalaria* sp.) and garden snails, including but not limited to brown garden snails, white garden snails (e.g., *Cantareus* sp., *Cornu* sp., *Theba* sp.), and/or slugs, including but not limited to gray garden slug (e.g., *Deroceras* sp.), the banded or three-band slug (e.g., *Lehmannia* sp), the tawny slug (e.g., *Limacus* sp), and the greenhouse slug (e.g., *Milax* sp) and (c) has a molecular weight selected from the group consisting of: about 540-550 and about 1280-1335 as determined by Liquid Chromatography/Mass Spectroscopy (LC/MS). These compositions may be formulated into compositions which may be used to control molluscs, particularly members of the Gastropoda and/or Bivalvia classes and more particularly mussels, snails and slugs. In one embodiment, the compound: (a) is obtainable from a microorganism, particularly a *Pseudomonas* sp.; (b) is toxic to a member of a class of molluscs selected from the group consisting of Bivalvia, particularly, mussels (e.g., *Dreissana* sp.) and/or Gastropoda, particularly, snails, which includes but is not limited to aquatic snails (e.g., *Biomphalaria* sp.) and garden snails, including but not limited to brown garden snails, white garden snails (e.g., *Cantareus* sp., *Cornu* sp., *Theba* sp.), and/or slugs, including but not limited to gray garden slug (e.g., *Deroceras* sp.), the banded or three-band slug (e.g., *Lehmannia* sp), the tawny slug (e.g., *Limacus* sp), and the greenhouse slug (e.g., *Milax* sp); (c) has a molecular weight of about 1280-1310 and more particularly, 1295 as determined by Liquid Chromatography/Mass Spectroscopy (LC/MS); (d) has 1H NMR values of δ 9.25, 8.36, 8.06, 7.82, 7.71, 7.52, 7.45, 6.82, 6.36, 6.08, 5.42, 5.39, 5.30, 5.14, 4.68, 4.42, 4.31, 4.16, 4.11, 4.07, 3.95-3.86, 3.83, 3.72, 3.66, 3.53, 3.48, 3.37, 3.17, 3.06, 2.56, 2.53, 2.45, 2.32, 2.21, 2.02, 1.96, 1.84, 1.72, 1.65, 1.61, 1.51, 1.48-1.37, 1.32, 1.12, 0.94, 0.91, 0.68; (d) has a High Pressure Liquid Chromatography (HPLC) retention time of about 50-55 minutes, more specifically about 52 minutes and even more specifically about 51.66 min on a reversed phase C-18 HPLC (e.g., Thermo Scientific, Hydersil Gold, 100×10 mm) column using a water:acetonitrile ($CH_3CN$) with a gradient solvent system (0-10 min; 30-40% aqueous $CH_3CN$, 10-20 min; 40-60% aqueous $CH_3CN$, 20-60 min; 60-80% aqueous $CH_3CN$, 60-65 min; 80-100% aqueous $CH_3CN$) at 2.5 mL/min flow rate and UV detection of 210 nm.

In another embodiment, the compound has the following characteristics: (a) is obtainable from a microorganism, particularly a *Pseudomonas* sp.; (b) is toxic to a member of a class of molluscs selected from the group consisting of Bivalvia, particularly, mussels (e.g., *Dreissana* sp.) and/or Gastropoda, particularly, snails, which includes but is not limited to aquatic snails (e.g., *Biomphalaria* sp.) and garden snails, including but not limited to brown garden snails, white garden snails (e.g., *Cantareus* sp., *Cornu* sp., *Theba* sp.), and/or slugs, including but not limited to gray garden slug (e.g., *Deroceras* sp.), the banded or three-band slug (e.g., *Lehmannia* sp), the tawny slug (e.g., *Limacus* sp), and the greenhouse slug (e.g., *Milax* sp); (c) has a molecular weight of about 1310-1335 and more particularly, 1321 as determined by LC/MS; (d) has a HPLC retention time of about 55-60 minutes, more particularly about 60 minutes and even more particularly 59.61 min on a reversed phase C-18 (Thermo Scientific, Hydersil Gold, 100×10 mm) HPLC column using an acetonitrile:water gradient using a water:acetonitrile ($CH_3CN$) with a gradient solvent system (0-10 min; 30-40% aqueous $CH_3CN$, 10-20 min; 40-60% aqueous $CH_3CN$, 20-60 min; 60-80% aqueous $CH_3CN$, 60-65 min; 80-100% aqueous $CH_3CN$) at 2.5 mL/min flow rate and UV detection of 210 nm. In yet another embodiment, the invention is directed to an isolated compound having the following characteristics (a) is obtainable from a microorganism, particularly, a *Pseudomonas* sp.; (b) is toxic to a member of a class of molluscs selected from the group consisting of Bivalvia, particularly, mussels (e.g., *Dreissana* sp.) and/or Gastropoda, particularly, snails, which includes but is not limited to aquatic snails (e.g., *Biomphalaria* sp.) and garden snails, including but not limited to brown garden snails, white garden snails (e.g., *Cantareus* sp., *Cornu* sp., *Theba* sp.), and/or slugs, including but not limited to gray garden slug (e.g., *Deroceras* sp), the banded or three-band slug (e.g., *Lehmannia* sp), the tawny slug (e.g., *Limacus* sp), and the greenhouse slug (e.g., *Milax* sp); (c) has a molecular weight of about 540-550 and more particularly, about 546 as determined by LC/MS; (d) has an HPLC retention time of about 50-55 minutes, more particularly, about 52 minutes and even more particularly, about 51.54 min on a reversed phase C-18 HPLC column (Phenomenex, luna C 18(2) 10 μL, 100 Å Axia, A250×30 mm) using a water:acetonitrile gradient solvent system (0-10 min; 35-45% aqueous $CH_3CN$, 10-20 min; 45-60% aqueous $CH_3CN$, 20-50 min; 60-85% aqueous $CH_3CN$, 50-60 min; 85-100% aqueous $CH_3CN$, 60-70 min; 100% $CH_3CN$) at 10 mL/min flow rate and UV detection of 210 nm.

The invention is further directed to a method for obtaining the compound(s) of the present invention comprising
(a) obtaining a suspension of cells derived from a *Pseudomonas* species and
(b) isolating the compound by chromatographic methods from said suspension The invention is further directed to compositions comprising said compounds as well as a composition comprising a water: acetonitrile solvent system (0-10 min; 35-45% aqueous $CH_3CN$, 10-20 min; 45-60% aqueous $CH_3CN$, 20-50 min; 60-85% aqueous $CH_3CN$, 50-60 min; 85-100% aqueous $CH_3CN$, 60-70 min; 100% $CH_3CN$) at 10 mL/min flow rate and UV detection of 210 nm fraction obtainable from a *Pseudomonas* species cell suspension by HPLC with a retention time of about 45-50 min, said fraction comprising at least two compounds that (a) are toxic to a member of a class of molluscs selected from the group consisting of Bivalvia, particularly, mussels (e.g., *Dreissana* species) and/or Gastropoda, particularly, snails, which includes but is not limited to aquatic snails (e.g., *Biomphalaria* species) and garden snails, including but not limited to brown garden snails, white garden snails (e.g., *Cantareus* sp., *Cornu* sp., *Theba* sp.), and/or slugs, including but not limited to gray garden slug (e.g., *Deroceras* sp.), the banded or three-band slug (e.g., *Lehmannia* sp), the tawny slug (e.g., *Limacus* sp), and the greenhouse slug (e.g., *Milax* sp); (b) have molecular weights between about 630-660 and between about 970-1000 as determined by LC/MS.

The invention relates a method for controlling one or more molluscs in a location where control is desired comprising introducing into said location at least one of (a) a cell suspension or extract derived from *Erwinia* sp. cells; (b) one or more compounds, wherein said compounds are lactone, lactam, carbamate, carboxylic acid and/or amide compounds or composition comprising said compounds, with the proviso that said compounds are not gamma-octalactone, gamma-nonalactone, gamma-decanolactone, gamma-undecalactone, N-cyclpentylcinnamamide, N-(trans-cinnamoyl)pyrrolidine, N-(trans-Cinnamoyl) piperidine and N-(trans-Cinnamoyl) hexamethyleneimine, 4-hydroxydodecanoic acid and dodecanoic acid and with the proviso that the composition is not a *Pseudomonas* culture, extract or suspension; (c) one or more compounds obtainable or derived from (i) *Pseudomonas* species, (ii) is toxic to a member of a class of molluscs selected from the group consisting of Bivalvia, particularly, mussels (e.g., *Dreissana* sp.) and/or Gastropoda, particularly, snails, which includes but is not limited to aquatic snails (e.g., *Biomphalaria* sp.) and garden snails, including but not limited to brown garden snails, white garden snails (e.g., *Can-

*tareus* sp., *Cornu* sp., *Theba* sp.), and/or slugs, including but not limited to gray garden slug (e.g., *Deroceras* sp.), the banded or three-band slug (e.g., *Lehmannia* sp), the tawny slug (e.g., *Limacus* sp), and the greenhouse slug (e.g., *Milax* sp) and (iii) has a molecular weight selected from the group consisting of: about 540-550 and about 1280-1335 as determined by Liquid Chromatography/Mass Spectroscopy (LC/MS); (d) a composition comprising a water: acetonitrile solvent system (0-10 min; 35-45% aqueous $CH_3CN$, 10-20 min; 45-60% aqueous $CH_3CN$, 20-50 min; 60-85% aqueous $CH_3CN$, 50-60 min; 85-100% aqueous $CH_3CN$, 60-70 min; 100% $CH_3CN$) at 10 mL/min flow rate and UV detection of 210 nm fraction obtainable from a *Pseudomonas* species cell suspension by HPLC with a retention time of about 45-50 min, said fraction comprising at least two compounds that (i) are toxic to a member of a class of molluscs selected from the group consisting of Bivalvia, particularly, mussels (e.g., *Dreissana* sp.) and/or Gastropoda, particularly, snails, which includes but is not limited to aquatic snails (e.g., *Biomphalaria* sp.) and garden snails, including but not limited to brown garden snails, white garden snails (e.g., *Cantareus* sp., *Cornu* sp., *Theba* sp.), and/or slugs, including but not limited to gray garden slug (e.g., *Deroceras* sp), the banded or three-band slug (e.g., *Lehmannia* sp), the tawny slug (e.g., *Limacus* sp), and the greenhouse slug (e.g., *Milax* sp); (ii) have molecular weights between about 630-660 and between about 970-1000 as determined by LC/MS, in amounts effective to control said molluscs in said location. This control may in one embodiment be achieved by inducing death in one or more molluscs comprising contacting said molluscs with the compounds set forth above. The molluscs may be contacted in a body of water or solid surface. Similarly, the invention is directed to the use of the above-referenced compounds, suspensions and compositions for formulating a composition for use in controlling mollusks, such as Gastropoda and Bivalvia in a location.

In a related aspect, the invention further relates to compositions for controlling one or more molluscs, particularly mussels and/or snails (e.g., white and/or brown garden snails, aquatic snails) and/or slugs in a location where control is desired and/or inducing death in one or more molluscs, particularly mussels and/or snails (e.g., white and/or brown garden snails, aquatic snails) and/or slugs in said location comprising one or more lactones, lactams, carbamates, carboxylic acids and/or amides, again with the proviso that said compound is not gamma-octalactone, gamma-nonalactone, gamma-decanolactone, gamma-undecalactone, N-cyclpentylcinnamamide, N-(trans-cinnamoyl)pyrrolidine, N-(trans-Cinnamoyl) piperidine and N-(trans-Cinnamoyl)hexamethyleneimine, 4-hydroxydecanoic acid and decanoic acid and with the proviso that the composition is not a *Pseudomonas* culture, extract or suspension.

In a particular embodiment, the invention is directed to a method for controlling one or more molluscs, particularly mussels and/or snails (e.g., white and/or brown garden snails, aquatic snails) and/or slugs, said method comprising the steps of:

(a) preparing a cell suspension or extract derived from *Erwinia* sp. cells; and (b) introducing said suspension or extract into a location where control is desired in an amount effective to control said molluscs.

*Erwinia* extracts may contain active ingredients set forth above, such as lactones and amides. Similarly the cell suspension or extract derived from *Erwinia* sp. cells may be formulated into compositions for use in controlling molluscs, particularly a class of molluscs selected from the group consisting of Bivalvia, particularly, mussels (e.g., *Dreissana* sp.) and/or Gastropoda, particularly, snails, which includes but is not limited to aquatic snails (e.g., *Biomphalaria* sp.) and garden snails, including but not limited to brown garden snails, white garden snails (e.g., *Cantareus* sp., *Cornu* sp., *Theba* sp.), and/or slugs, including but not limited to gray garden slug (e.g., *Deroceras* sp.), the banded or three-band slug (e.g., *Lehmannia* sp), the tawny slug (e.g., *Limacus* sp), and the greenhouse slug (e.g., *Milax* sp).

The invention is further directed to a composition comprising at least one or more substances effective for controlling one or more molluscs, particularly a class of molluscs selected from the group consisting of Bivalvia, particularly, mussels (e.g., *Dreissana* sp.) and/or Gastropoda, particularly, snails, which includes but is not limited to aquatic snails (e.g., *Biomphalaria* sp.) and garden snails, including but not limited to brown garden snails, white garden snails (e.g., *Cantareus* sp., *Cornu* sp., *Theba* sp.), and/or slugs, including but not limited to gray garden slug (e.g., *Deroceras* sp.), the banded or three-band slug (e.g., *Lehmannia* sp), the tawny slug (e.g., *Limacus* sp), and the greenhouse slug (e.g., *Milax* sp), and optionally an inert material preferably for use in controlling one or more mollucs. The substance may be derived from chlorine or a *Pseudomonas* species, more particularly derived from *Pseudomonas fluorescens* or alternatively an organism (e.g., a *Pseudomonas* strain) having the identifying characteristics of *Pseudomonas* ATCC 55799. In another particular embodiment, the composition may comprise a substance that is a cell suspension derived from a *Pseudomonas* species (e.g., *P. fluorescens*) and even in a more particular embodiment, the cell suspension may comprise cells having the toxin producing characteristics of *Pseudomonas* ATCC 55799. In yet another particular embodiment, the substances in said composition may be one or more toxins derived from isolated from a *Pseudomonas* species or alternatively derived from an organism having the identifying characteristics of *Pseudomonas* ATCC 55799. The composition may alternatively comprise the compounds used in the method of the present invention set forth above as well as the compounds of the present invention set forth above and may be used to control a member of a Gastropoda and Bibalvia class. The inert material may be a clay mineral (kaolinite, smectite, attapulgite). The invention is further directed to a method for controlling one or more molluscs, particularly, mussels and/or snails (e.g., aquatic, garden snails and/or slugs in a location where control is desired comprising introducing in said location a substance effective for controlling said molluscs and optionally one or more inert materials in amounts effective to control said molluscs in said location containing said molluscs. In particular, the substance for controlling said molluscs is present in an amount effective to result in at least about a 20% mortality relative to untreated control, typically about 50-95% and said inert material is present in an amount sufficient or effective to increase mortality rate of said substance for controlling said molluscs at least about 20%, typically 25-40%. In a particular embodiment, the inert material is introduced into said location prior to introduction of the substance for controlling said molluscs; in a more particular embodiment, the inert material is introduced at least about one hour prior to the introduction of the substance. In another particular embodiment, the inert material is introduced into the location simultaneously with the substance for controlling molluscs set forth above, particularly mussels, snails and/or slugs.

In a related aspect, the invention is directed to the use of an inert material for increasing the efficacy of one or more substances for controlling one or more molluscs, particularly a class of molluscs selected from the group consisting of Bivalvia, particularly, mussels (e.g., *Dreissana* sp.) and/or Gastropoda, particularly, snails, which includes but is not limited to aquatic snails (e.g., *Biomphalaria* sp.) and garden snails, including but not limited to brown garden snails, white garden snails (e.g., *Cantareus* sp., *Cornu* sp., *Theba* sp.), and/or slugs, including but not limited to gray garden slug (e.g., *Deroceras* sp.), the banded or three-band slug (e.g., *Lehmannia* sp), the tawny slug (e.g., *Limacus* sp), and the greenhouse slug (e.g., *Milax* sp), in a location where control is desired. The location may be a liquid (e.g., a body of water or paint) or solid surface, such as plastic, concrete, wood, fiberglass, pipes made of iron and polyvinyl choride, surfaces covered with coating materials and/or paints. In particular, the invention is directed to a method for increasing the efficacy of one or more substances for controlling one or more of said molluscs, particularly a class of molluscs selected from the group consisting of Bivalvia, particularly, mussels (e.g., *Dreissana* sp.) and/or Gastropoda, particularly, snails, which includes but is not limited to aquatic snails (e.g., *Biomphalaria* sp.) and garden snails, including but not limited to brown garden snails, white garden snails (e.g., *Cantareus* sp., *Cornu* sp., *Theba* sp.), and/or slugs, including but not limited to gray garden slug (e.g., *Deroceras* sp), the banded or three-band slug (e.g., *Lehmannia* sp), the tawny slug (e.g., *Limacus* sp), and the greenhouse slug (e.g., *Milax* sp), comprising introducing in a location where control is desired one or more inert materials in amounts effective to increase efficacy of said substance when introduced in said location. In a particular embodiment, these inert materials increases the efficacy of said substances at least about 20%.

Further, the invention relates to an antifouling paint comprising an antivegative, biocidal effective amount of the compositions and compounds of the present invention in a paint carrier. The invention further relates to the use of the compounds and compositions of the present invention in formulating such an antifouling paint.

DETAILED DESCRIPTION OF THE INVENTION

Figure 1A:
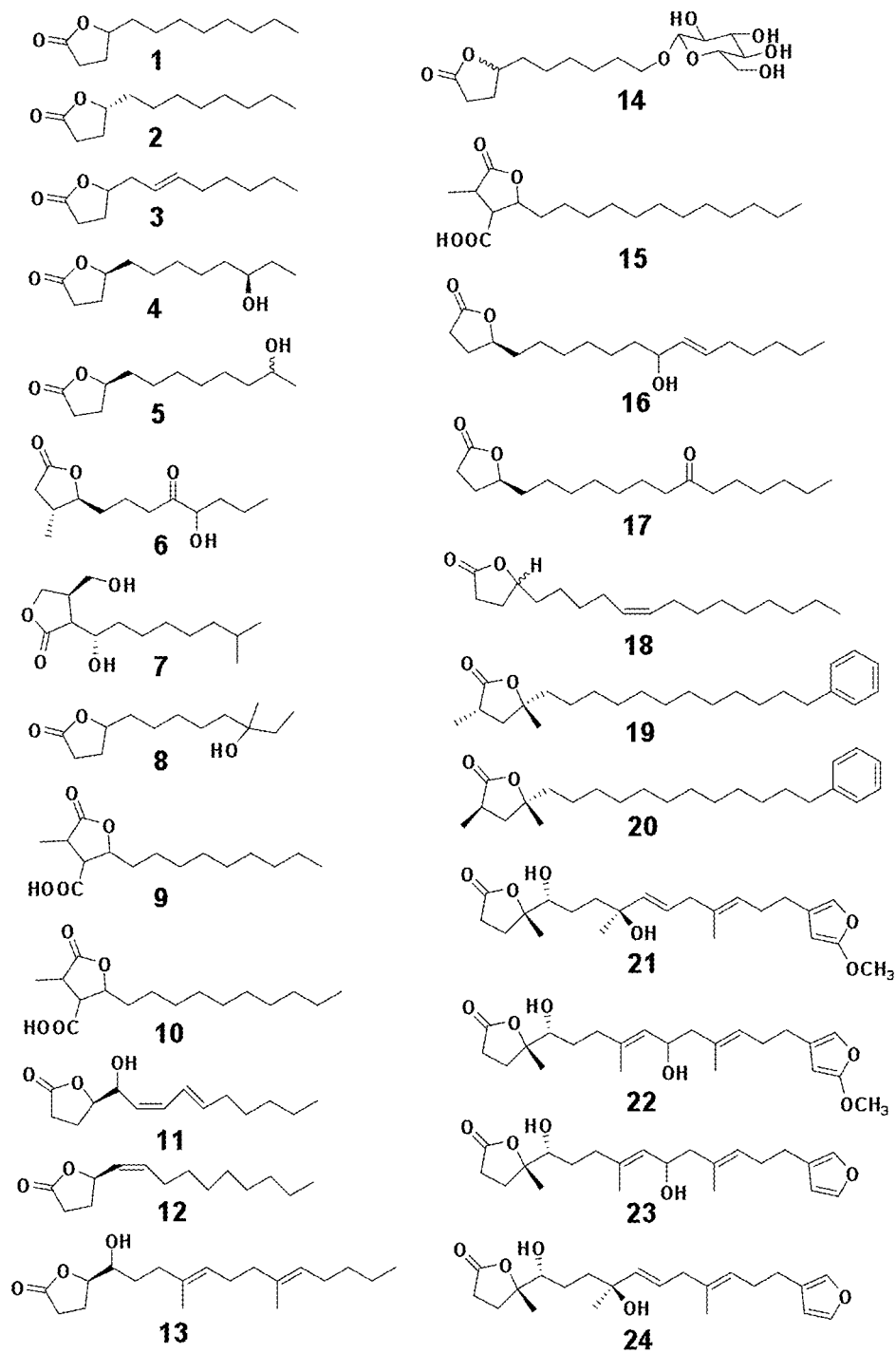
FIGS. 1*a* and 1*b* shows structures of natural products used in the method of the present invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As defined herein, "controlling mussels" means controlling the eggs, larvae, veligers and post-veligers of the mussel by killing or disabling them so that they cannot colonize in a give location.

As defined herein, "derived from" means directly isolated or obtained from a particular source or alternatively having identifying characteristics of a substance or organism isolated or obtained from a particular source.

As used hereafter, the term "alkyl" refers to a saturated hydrocarbon radical which may be straight-chain or branched-chain (e.g., ethyl, isopropyl, t-amyl, or 2,5-dimethylhexyl, etc.). This definition applies both when the term is used alone and when it is used as part of a compound term.

The terms "cycloalkyl" and "cycloalkenyl" refer to a saturated hydrocarbon ring and includes bicyclic and polycyclic rings. Similarly, cycloalkyl and cycloalkenyl groups having a heteroatom (e.g., N, O, or S) in place of a carbon ring atom may be referred to as "heterocycloalkyl", "heterocyclyl," and "heterocycloalkylene," respectively.

The term "alkenyl" as used herein refers to an alkyl group as described above which contains one or more sites of unsaturation that is a double bond. Similarly, the term "alkynyl" as used herein refers to an alkyl group as described above which contains one or more sites of unsaturation that is a triple bond.

The term "alkoxy" refers to an alkyl radical as described above which also bears an oxygen substituent which is capable of covalent attachment to another hydrocarbon radical (such as, for example, methoxy, ethoxy, aryloxy, and t-butoxy).

The term "aryl" refers to an aromatic carbocyclic substituent which may be a single ring or multiple rings which are fused together, linked covalently or linked to a common group such as an ethylene or methylene moiety. Similarly, aryl groups having a heteroatom (e.g., N, O, or S) in place of a carbon ring atom are referred to as "heteroaryl."

The terms "arylalkyl," "arylalkenyl," and "aryloxyalkyl" refer to an aryl radical attached directly to an alkyl group, an alkenyl group, or an oxygen atom which is attached to an alkyl group, respectively. For brevity, aryl as part of a combined term as above is meant to include heteroaryl as well.

The term "hetero" as used in a "heteroatom-containing alkyl group" (i.e., a "heteroalkyl" group) or a "heteroatom-containing aryl group" (i.e., a "heteroaryl" group) refers to a molecule, linkage, or substituent in which one or more carbon atoms are replaced with an atom other than carbon, e.g., nitrogen, oxygen, sulfur, phosphorus, or silicon.

As defined herein, "derived from" and "obtainable from" means directly isolated or obtained from a particular source or alternatively having identifying characteristics of a substance or organism isolated or obtained from a particular source. These terms are used interchangeably throughout the specification.

As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods, electrophoretic methods.

Compounds

The compounds used in the compositions and methods of the present invention may be members of the following three families.

Family I Compounds

In a particular embodiment, family I possesses following chemical structures:

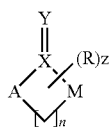

Where X includes, but is not limited to carbon, sulfur, phosphorus; Y includes, but is not limited to sulfur, oxygen; A and M include, but are not limited to carbon, oxygen, nitrogen, sulfur and n is 1 to 21 Where (R)z represents number Z of the number of substituents on the group R on the ring. R and the substituents on R may be a hydrogen, hydroxyl, alkyl hydroxyl, alkenyl hydroxyl, alkynyl hydroxyl, alkyloxy, alkenyloxy, alkynyloxy, cycloalkyl, cycloalkenyl, alkyl, alkenyl, alkynyl, heterocyclyl, heteroaryl, aromatic, aryl group, NH-substituted, or N,N-substituted group or any other substituted group. The length of the one of the substituted R chains can be from 1 to 25 atoms, the preferred length will be from 7 to 17 atoms; The number Z can be 0, 1, 2, 3 until n+2, preferred z=0, 1, 2, 3.

In a particular embodiment, the compound may be derived from *Pseudomonas fluorescens* and has a hydroxylated unsaturated fatty acid lactone structure comprising at least one lactone moiety which is a 5 membered γ-lactone, at least one unsaturated moiety and at least one alcohol group; a molecular weight from 285 to about 310 in the core structure; at least 15 carbons and at least 3 oxygens. In a more particular embodiment, the compound may have the structure

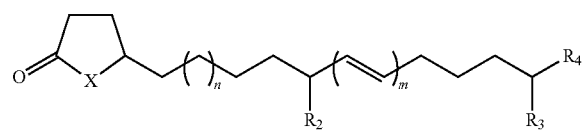

wherein: X are each independently —O, —NR$_1$, or —S, wherein R$_1$ is —H or C$_1$-C$_6$ alkyl; n=0 to 15, R$_2$ to R$_4$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=double bond or triple bond. In yet another particular embodiment, Y and M are oxygen, A and X are carbon and n is 2 or 3, R is a C7 or C8 alkyl and z is 0, wherein when n is 2 and R is a C7 alkyl, R is attached to A.

Figure 1B:
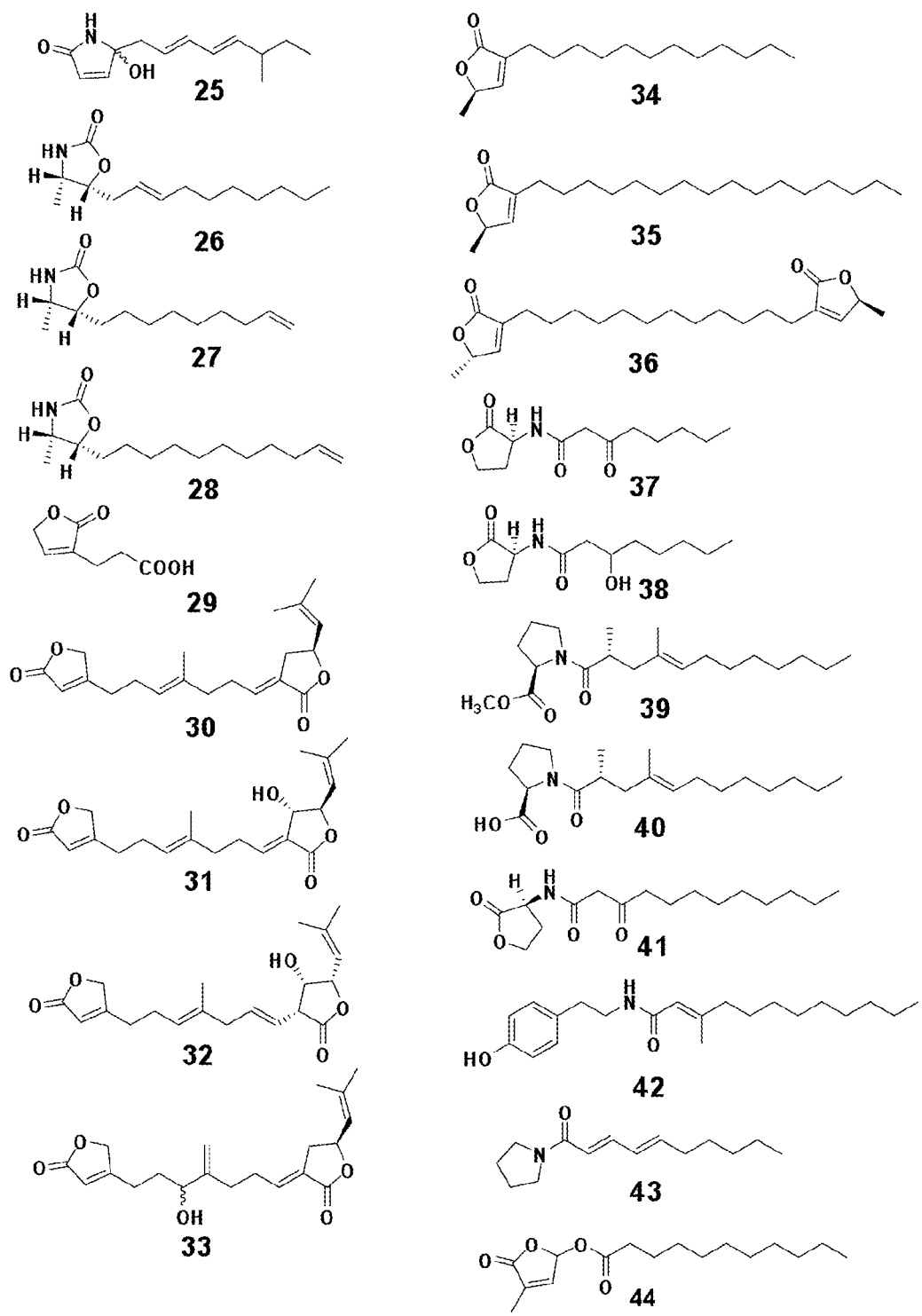
Figure 2:
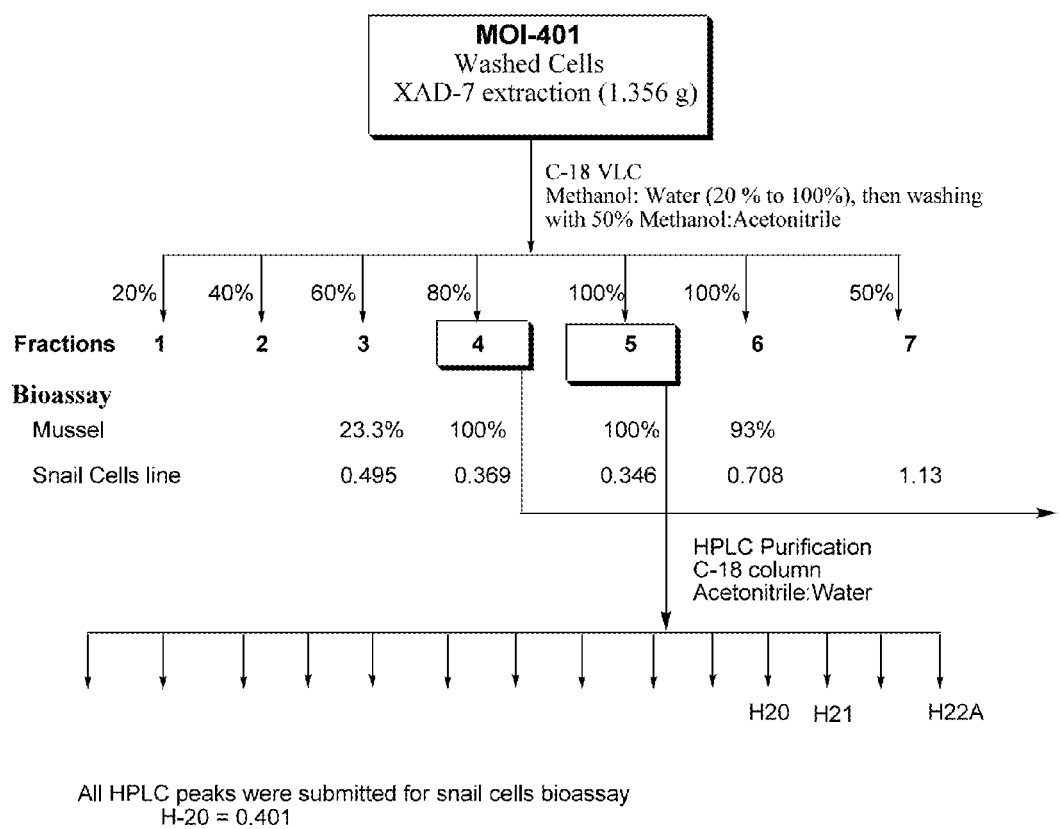
FIG. 2 shows the scheme for isolating the active fractions.

In an even another particular embodiment, Family I compounds may be the compounds set forth in 1 to 28 (FIGS. 1a and 1b). These are from either natural materials or compounds obtained from commercial sources or by chemical synthesis. Natural sources of Family I compounds include, but are not limited to plants, corals, microorganisms, sponges and animals. In a more particular embodiment, plants which include the Family I compounds include but are not limited to, or alternatively, Family I compounds may be derived from species such as *Myoporum bontioides* (compound 14) [Moe Kanemoto, et al., Chlorine-containing iridoid and iridoid glucoside, and other glucosides from leaves of *Myoporum bontioides*, Phytochemistry 69 (2008) 2517-2522], *Micromelum hirsutum* (compound 18) [Ma, G. Y. et al. anti-tuberculosis constituents from the stem bark of *Micromelum hirsutum*, Planta Med. 2005, 71, 261-267], Family I compounds may also be derived from microorganisms including but not limited to *Antrodia camphorate* (compounds 4, 5) [Shao, Y. Y. et al., Chemical constituents of *Antrodia camphorate* submerged whole broth, Natural Product Research, 2008, 22 (13) 1151-1157], *Saccharomyces cerevisiae* (compound 2) [Gocho, S. et al. Biotransformation of oleic acid to optically active γ-dodecalactone, Biosci. Biotech. Biochem. 1995, 59 (8) 1571-1572], *Mesorhizobium* sp. (compounds 2, 17) [Wei, G. H. et al., Rhizobialide: A New Stearolactone Produced by *Mesorhizobium* sp. CCNWGX022, a Rhizobial Endophyte from *Glycyrrhiza uralensis*, Chemistry and Biodiversity, 2007, 4, 893-898], *Ophiostoma* piliferum (compound 16), [Wei, G. H. et al., Rhizobialide: A New Stearolactone Produced by *Mesorhizobium* sp. CCNWGX022, a Rhizobial Endophyte from *Glycyrrhiza uralensis*, Chemistry and Biodiversity, 2007, 4, 893-898], *Streptomyces* sp. (compound 8) [Khaled A. Shaaban, Mohamed Shaaban, Petrea Facey, Serge Fotso, Holm Frauendorf, Elisabeth Helmke, Armin Maier, Heinz H. Fiebig, Hartmut Laatsch, Electrospray Ionization Mass Spectra of Piperazimycins A and B and γ-Butyrolactones from a Marine-derived *Streptomyces* sp. J. Antibiot. 61(12): 736-746, 2008], *Macrophomina phaseolzna* (compounds 9, 10 & 15) [Shashib, Mahat et al., structure and stereochemistry of phaseolinic acid: a new acid from *Macrophomina phaseolzna*, Journal of Natural products, 1987, 50 (2) 245-247], *Sporidiobolus salmonicolor* (compounds 1, 3) [Laurent Dufosse, et al., Chirality of the γ-Lactones Produced by *Sporidiobolus salmonicolor* Grown in Two Different Media, Chirality, 1997, 667-671] and *Streptomyces* (compound 7) [Shohei Sakuda, et al., Biosynthetic Studies on *Virginiae* Butanolide A, a Butyrolactone Autoregulator from *Streptomyces*. Part 2, Preparation of Possible Biosynthetic Intermediates and Conversion Experiments in a Cell-free System. J. Chem. Soc. Perkin Trans. I 1993, 2309-2315].

In an additional particular embodiment, Family I compounds may be derived from sponges such as *Haliclona* n. sp (compounds 26, 27 & 28) [Richard J. Clark, Mary J. Garson, and John N. A. Hooper, Antifungal Alkyl Amino Alcohols from the Tropical Marine Sponge *Haliclona* n. sp. J. Nat. Prod. 2001, 64, 1568-1571], *Axinellas* sp (compound 25) [Miller, W. F. Tinto, J.-P. Yang, S. McLean and W. F. Reynolds, Axinellamide, a new alkaloid from the marine sponge *Axinellas* sp. Tetrahedron Lett., 1995, 36, 5851], *Plakortis nigra* (compounds 19-20) [Joel S. Sandler, et al., Cytotoxic β-Carbolines and Cyclic Peroxides from the Palauan Sponge *Plakortis nigra*, J. Nat. Prod. 2002, 65, 1258-1261] and *Ircinia formosana* (compounds 21-24) [Shen, Y. C. et al., Novel linear C22-sesterterpenoids from sponge *Ircinia formosana*, Tetrahedron Letters 47 (2006) 4007-4010]. Compounds 26-28 are examples of carbamates.

In another particular embodiment, Family I compounds may be derived from corals including but not limited to *Sarcophyton trocheliophorum* and *Lithophyton arboretum* (compounds 11 & 13) [Tomas Rezanka, et al., γ-lactones from the soft corals *Sarcophyton trocheliophorum* and *Lithophyton arboretum*, Tetrahedron, 2001, 57, 8743-8749]. In yet another particular embodiment, insects which include the Family I compounds may be derived from insects including but not limited to Female Japanese Beetle Sex Pheromone (compound 12) [J. H. Tumlinson, Identification of the Female Japanese Beetle Sex Pheromone Inhibition of Male Response by an Enantiomer, Science, 1977, 197, 789-792] and insect toxins (compound 6) [John A. Findlay, et al., Insect toxins from spruce endophytes, Can. J. Chem. 2003, 81, 284-292].

Family I compounds may also include but are not limited to gamma-dodecalactone, delta-tridecalactone, piliferolide A and alpha-heptyl-gamma-butyrolactone set forth in the Examples. These may be obtained by synthetic methods using procedures known in the art or from commercial sources.

Family II Compounds

In another particular embodiment, family II possesses following chemical structures:

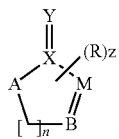

Where X is carbon; Y is oxygen; A, B and M are carbon, oxygen, nitrogen, sulfur or other atoms and n is 1 to 21.

Where (R)z represents number Z of the number of substituents on the group R on the ring. R and the substituents on R may be a hydrogen, hydroxyl, alkyl hydroxyl, akenyl hydroxyl, alkynyl hydroxyl, alkyloxy, alkenyloxy, alkynylxoy, cycloalkyl, cycloalkenyl, alkyl, alkenyl, alkynyl, heterocyclyl, heteroaryl, aromatic, aryl group, NH-substituted, or N,N-substituted group or any other substituted group. The length of the one of the substituted R chain can be from 1 to 25 atoms, with the preferred length being from 7 to 17 atoms. The number Z can be 0, 1, 2, 3 until n+2, preferred z=0, 1, 2, 3.

In a particular embodiment, Family II compounds such as compounds from 29 to 36 and 44 (see FIGS. 1a and 1b) may be derived from natural sources, chemical synthesis or commercial sources. Natural sources of Family II compounds include, but are not limited to plants, corals, microorganisms, sponges and animals. In a particular embodiment, examples of such plants include, but are not limited the following species such as *Heteroplexis micocephala* (compounds 30, 31, 32 & 33) [Fan, X. N., et al., Chemical Constituents of Heteroplexis micocephala. J. Nat. Prod. 2009, 72, 1184-1190] and *Iryanthera* species (compound 34) [Vieira, P. C., et al., γ-Lactones from *Iryanthera* species, Phytochemistry, 1983, 22 (3) 711-713] and *Litse verticillata* (compound 44) [Zhang, H. J. et al., sesquiterpenes and butenolides, natural anti-HIV constituents from *Litse verticillata*, Planta Med, 2005, 71, 452-457]. In a more particular embodiment, sources microorganisms which include the Family II compounds include, but are not limited the following species such as *Streptomyces rishiriensis* A-5969 (compound 29) [Yumiko Itoh, Hiroshi Shimura, Mayumito, NaoHaru Watanabe, Michio Yamagishi, Masaharu Tamai and Kazunori Hanada, novel hepatoprotective 7-lactone, MH-031, Discovery, Isolation, Physical-Chemical properties and structural elucidation, The Journal of antibiotics, 1991, 44 (8) 832-837. In a more particular embodiment, corals which include the Family II compounds include, but are not limited to the following species such as *Pterogorgia anceps* (compound 35) [Guo, Y. W. et al., Three New Butenolide Lipids from the Caribbean Gorgonian *Pterogorgia anceps*, J. Nat. Prod. 1999, 62, 1194-1196; Manuel Lorenzo et al., 13C NMR-Based Empirical Rules to Determine the Configuration of Fatty Acid Butanolides. Novel γ-Dilactones from *Pterogorgia* spp, Organic Letters, 8 (22) 5001-5004] and *Pterogorgia citrine* (compound 36) [Abimael D. Rodriguez et al., further butenolides from the Caribbean octocoral *Pterogorgia citrine*, Journal of Natural Products, 1994, 57(3) 339-347].

Family III Compounds

In another particular embodiment, family III compounds possess the following chemical structure:

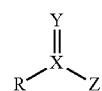

Wherein X is carbon; Y is oxygen; Z is hydrogen, hydroxyl, alkenyl hydroxyl, alkynyl hydroxyl, alkyl, alkenyl, alkynyl, heterocyclyl, aromatic, aryl group, NH-substituted, or N,N-substituted group or any other substituted group.

Wherein R is alkenyl hydroxyl, alkynyl hydroxyl, alkyl, alkenyl, alkynyl, heterocyclyl, aromatic, aryl group, NH-substituted, or N,N-substituted group or any other substituted group. The length of R chain can be from 1 to 50, preferred from 7 to 17.

In a particular embodiment, Family III compounds such as compounds from 37 to 43 (FIGS. 1a and 1b) may be derived from natural or commercial sources or by chemical synthesis. Natural sources of Family III compounds include, but are not limited to plants, corals, microorganisms, sponges and animals. In a more particular embodiment, plants sources include, but are not limited to *Piper* spp (compound 43) [Likhitwitayawuid, K., Ruangrungsi, N, Lange, G and Decicco, C., Structural Elucidation and Synthesis of New Components isolated from *Piper Samentosum*, Tetrahedron 1987 (43) 3689-3694; Kiuchi, F., Nakamura, N., Tsuda, Y., Kondo, K and Yoshimura, H. Studies on Crude Drugs Effective on Visceral Larva Migrans. IV. Isolation and Identification of Larvicidal Principles in Pepper Chemical and Pharmaceutical Bulletin 1988(36):2452]. In a more particular embodiment, corals include, but are not limited to *Plexaura flava* (compound 42) [B. N. Ravi, et al., Lipid and Terpenoid Metabolites of the Gorgonian *Plexaura flava*, Aust. J. Chem., 1982, 35, 105-12] and In a more particular embodiment, microorganisms which include the Family III compounds include, but are not limited the following species such as *Lyngbya majuscula* and *Schizothrix calcicola* (compound 39, 40) [George G. Harrigan, et al., Tumonoic Acids, Novel Metabolites from a Cyanobacterial Assemblage of *Lyngbya majuscula* and *Schizothrix calcicola*, J. Nat. Prod. 1999, 62, 464-467], *Pseudomonas aeruginosa* (compound 41) [Michael, K. Winson., et al. Multiple N-acyl-L-homoserine lactone signal molecules regulate production of virulence determinants and secondary metabolites in *Pseudomonas aeruginosa*, Proc. Natl. Acad. Sci. USA, 1995, 92, 9427-9431], *Erwinia carotovora* (compound 37) [Gu nter Brader, Solveig Sjoblom, Heidi Hyytia inen, Karen Sims-Huopaniemi, and E. Tapio Palva, Altering Substrate Chain Length Specificity of an Acylhomoserine Lactone Synthase in Bacterial Communication, The Journal of Biological Chemistry, 2005, 280(11) 10403-10409] and *Photobacterium phosphoreum* (compound 38) [L. R. Flodgaard, P. Dalgaard, J. B. Andersen, K. F. Nielsen, M. Givskov, and L. Gram, Nonbioluminescent Strains of *Photobacterium phosphoreum* produce the Cell-to-Cell Communication Signal N-(3-Hydroxyoctanoyl)homoserine Lactone, Applied and Environmental Microbiology, 2005, 71(4), 2113-2120].

In yet another particular embodiment, the family III compounds may be a sarmentine analog having the following structure:

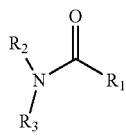

Wherein R1 is an alkyl, alkenyl, alkynyl, heterocyclyl, aromatic, aryl group, NH-substituted, or N,N-substituted group and the length of R1 chain is from 4 to 20 atoms, and preferably from 6 to 12 atoms.

Wherein R2 and R3 are alkyl, alkenyl, alkynyl, cycloalkyl, cycloalkenyl, aromatic, arylalkyl, heterocyclyl or heteroaryl; or alternatively R2+R3+N can be an N-containing heterocyclic moiety, Wherein when R2+R3+N is an N-containing heterocyclic moiety, R1 is an alkyl, alkenyl, alkynyl, heterocyclyl, NH-substituted, or N,N-substituted group.

In a most particular embodiment, the sarmentine analog is N-Cyclopentyldecanamide, N-(Decanoyl)pyrrolidine, N-(Decanoyl)piperidine, N-(Decanoyl)hexamethyleneimine, N-Cyclopentyldecenamide, (N-(Decenoyl)pyrrolidine, N-(Decenoyl)piperidine, N-(Decenoyl)hexamethyleneimine and N-(Decenoyl)piperidine.

The sarmentine analogs may be obtained using procedures known in the art which may include but is not limited to those set forth in application Ser. No. 61/227,412, filed Jul. 21, 2009.

In yet another particular embodiment, the compound may be derived from *Pseudomonas fluorescens* and characterized as having a hydroxylated unsaturated fatty acid structure comprising at least one carboxylic acid moiety, at least one unsaturated moiety and at least one alcohol group; molecular weight from 285 to about 310 in the core structure; at least 15 carbons and at least 3 oxygens.

In a more particular embodiment of the invention, there are provided compounds having the structure

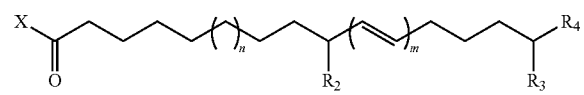

wherein: X are each independently —OH, —$NR_1$, or —S, wherein $R_1$ is —H or $C_1$-$C_6$ alkyl; n=0 to 15, $R_2$ to $R_4$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl; m=double bond, triple bond. In a most specific embodiment, the compound has the structure

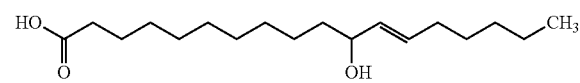 [SMILES: CCCCC/C=C/C(O)CCCCCCCCCC(=O)O]

Methods of Production

As noted above, the compounds and compositions of the present invention may be obtained, is obtainable or derived from an organism having the identifying characteristics of a *Pseudomonas* species, more particularly, from an organism having the identifying characteristics of a strain of *Pseudomonas fluorescens* or alternatively from an organism having the identifying characteristics of *Pseudomonas fluorescens* isolate, ATCC 55799 as set forth in U.S. Pat. No. 6,194,194. The methods comprise cultivating these organisms and obtaining the compounds and/or compositions of the present invention by isolating these compounds from the cells of these organisms.

In particular, the organisms are cultivated in a nutrient medium using methods known in the art. The organisms may be cultivated by shake flask cultivation, small scale or large scale fermentation (including but not limited to continuous, batch, fed-batch, or solid state fermentations) in laboratory or industrial fermentors performed in suitable medium and under conditions allowing cell growth. The cultivation may take place in suitable nutrient medium comprising carbon and nitrogen sources and inorganic salts, using procedures known in the art. Suitable media are available may be available from commercial sources or prepared according to published compositions. A particular embodiment is disclosed in the examples infra and in U.S. Pat. No. 6,194,194.

After cultivation, the cells may be concentrated and subsequently suspended in a buffer to obtain a cell suspension. The compounds and/or compositions of the present invention may be extracted from the suspension. The extract may be fractionated by chromatography. Chromatography may be assayed for toxic activity against molluscs, such as mussels, snails (e.g., aquatic and/or garden snails) and/or slugs, using methods known in the art; one particular embodiment is disclosed in the examples, infra. This process may be repeated one or more times using the same or different chromatographic methods.

The compounds of the present invention may also be obtained by synthetic methods. Alternatively, for peptide compounds, the compounds may be obtained by expressing nucleic acid sequences encoding these compounds in a recombinant DNA host using methods known in the art.

Formulations

The composition of the present invention may comprise a chemical or biopesticide product that is useful in controlling molluscs, particularly members of the Gastropoda and/or Bivalvia classes and more particularly mussels, snails and slugs. The invention is directed to isolated compounds obtainable or derived from (a) a microorganism such as a *Pseudomonas* species, more particularly, *Pseudomonas fluorescens* or alternatively, an organism having the identifying characteristics of *Pseudomonas* ATCC 55799; (b) is toxic to a member of a class of molluscs selected from the group consisting of Bivalvia, particularly, mussels (e.g., *Dreissana* species) and/or Gastropoda, particularly, snails, which includes but is not limited to aquatic snails (e.g., *Biomphalaria* species) and garden snails, including but not limited to brown garden snails, white garden snails (e.g., *Cantareus* species, *Cornu* species, *Theba* species), and/or slugs, including but not limited to gray garden slug (e.g., *Deroceras* sp.), the banded or three-band slug (e.g., *Lehmannia* sp), the tawny slug (e.g., *Limacus* sp), and the greenhouse slug (e.g., *Milax* sp) and (c) has a molecular weight selected from the group consisting of: about 540-550 and about 1280-1335 as determined by Liquid Chromatography/Mass Spectroscopy (LC/MS). These compositions may be formulated into compositions which may be used to control molluscs, particularly members of the Gastropoda and/or Bivalvia classes and more particularly mussels, snails and slugs.

Examples include but are not limited to chlorine and substances derived from a *Pseudomonas* species as described in for example U.S. Pat. No. 6,194,194. Furthermore, compounds disclosed above and used in the invention can be made into compositions (also alternatively referred to as "formulations") and can be formulated in any form. Non-limiting formulation examples include emulsifiable concentrates (EC), wettable powders (WP), soluble liquids (SL), aerosols, ultra-low volume concentrate solutions (ULV), soluble powders (SP), microencapsulation, water dispersed granules, flowables (FL), microemulsions (ME), nano-emulsions (NE), etc. In any formulation described herein, percent of active ingredient is within a range of 0.01% to 99.99%. In a particular embodiment, the formulations may be free of surfactants.

Examples of the inert material that may be used in the compositions of the present invention include, but are not limited to, inorganic minerals such as kaolin, mica, gypsum, phyllosilicates, carbonates, sulfates, or phosphates; or botanical materials such as wood products, cork, powdered corn cobs, rice hulls, peanut hulls and walnut shells. In a particular embodiment, the inert material can be obtained or derived from a clay mineral (kaolinite, smectite, attapulgite) suspended in water at a rate of about 1 to 20 mg/liter corresponding to approximately 1 to 20 NTU (normalized turbidity units). The inert materials used to enhance mussel siphoning can be applied in solid form or as a suspension in aqueous solution, preferably water, directly to the water or the location (e.g., solid surface) where the mussels are treated. In a particular embodiment, to enhance product efficacy, an inert material such as clay, silt, sediment or any other material with no nutritional value and with a small enough particle size can be suspended in water prior to the treatment with a chemical or a biopesticide product.

Methods of Use

The compounds and compositions of the present invention may be used to control molluscs, particularly, a member of the Gastropoda and/or Bivalvia class, more particularly mussels (e.g., *Dreissana* species) and/or Gastropoda, particularly, snails, which includes but is not limited to aquatic snails (e.g., *Biomphalaria* species) and garden snails, including but not limited to brown garden snails, white garden snails (e.g., *Cantareus* species, *Cornu* species, *Theba* species), and/or slugs, including but not limited to gray garden slug (e.g., *Deroceras* sp), the banded or three-band slug (e.g., *Lehmannia* sp), the tawny slug (e.g., *Limacus* sp), and the greenhouse slug (e.g., *Milax* sp) in a body of water or on surfaces where molluscs such as mussels, snails and/or slugs gather or alternatively as an anti-fouling agent in paint. In the event that it is used as an antifouling agent in paint, it is present in an anti-vegetative, biocidally effective amount. Surfaces where molluscs such as mussels, snails and/or slugs include but are not limited to plastic, concrete, wood, fiberglass, pipes made of iron and polyvinyl chloride and surfaces covered with paints and/or coatings. Coatings may be formulated from pigments, binders, additives, and/or carrier fluids and are preferably applied in a thin film to provide protection or decoration to a surface. The end product (which contains the active compound) will be used at 10-200 mg/L, more specifically at 25-100 mg/L (ppm) or 25-10000 mg/kg. It will be applied either as a dry product or suspended in water into pipes, dam structures, holding tanks, and open waters such as streams, rivers, lakes, irrigation canals, ponds and lakes through specific application pumps and mixing systems.

In a particular embodiment, the present invention is directed to a method for improving biopesticidal and pesticidal activity of materials used to control invasive molluscs, particularly mussels comprising the steps of:

1. suspension of inert material such as clay into the water to trigger the siphoning activity for about 1-24 hours before the chemical or biopesticide treatment
2. addition of a chemical or a biopesticide into the water at a desired level The invention is also directed to a method comprising a step of administering a microbial biopesticide in combination of an inert material such as clay to enhance the uptake and hence, mortality of mussels.

To activate the mussel siphoning, this clay (turbidity) treatment should be carried on for about 1 to 6 hours, usually about 3-4 hours, and for about 1 to 24 hours, typically about 14-18 hours before the treatment with a chemical/pesticide. Alternatively, the turbidity treatment can be applied simultaneously with the chemical or biopesticide treatment.

According to the one embodiment of this invention, treatment of molluscs, such as mussels, snails and slugs can be carried out in 500-mL glass jars or in a biobox constructed of acrylic sheets. In the glass jars, aeration during treatment is provided by airflow through aquarium air stones connected to nylon tubing. In the biobox, water is constantly flowing at a rate of 1 gallon per minute.

The materials for the turbidity treatment as well as for the chemical/biopesticide product can be mixed in the water by pipetting or via a peristaltic pump. In bioboxes, a more uniform mixing is achieved using a paddle mixer at the point of injection. The compositions of the present invention can be in a suitable form for direct application or as a concentrate or primary composition, which requires dilution with a suitable quantity of water or other diluent before application.

The effective amount of the turbidity materials will depend upon the application, water temperature, if applied to water, and duration of the treatment. In general, the composition may be applied at a rate of from about 1 to about 20 mg per liter; preferably at a rate of from about 5 to about 10 mg per liter so that the measured turbidity does not rise above 20 NTU.

EXAMPLES

The examples below are presented to describe preferred embodiments and utilities of the invention and is not meant to limit the invention unless otherwise stated in the claims appended hereto.

Example 1

Molluscicide Studies

Materials and Methods
1. Allow *quagga* mussels to acclimate in the small Petri dishes for 24 hrs.
   Pour the mussels into a Petri dish to determine if the mussels are alive or not. Toss out the dead and empty mussels.
   Count out 10 live/healthy mussels.
   Put 10 live/healthy mussels in each small Petri dish with hard water.
   Keep a separate plate of mussels. These are the "extra mussels" that will be used to replace dead or empty mussels after 24 hrs in the other experimental plates.
   Aeration is not needed due to the low volume of water (DO is high).

2. Day of mussel treatment:
Check the mussels (Use the rubber policemen at all times when checking the mussels. Only use the tweezers to remove dead mussels).
Count to make sure there are 10 live/healthy mussels per small Petri dish.
Get the sample(s) ready.
Dilute appropriately with hard water in a 50 ml falcon tube for each sample. Vortex to mix prior to dosing.
EX: 70 ppm, 2 reps per sample. Add 34 ml of hard water into the falcon tube. Add 51 ul of the sample into the same falcon tube with hard water. Vortex to mix prior to dosing.
3. Dosing:
Vortex the sample prior to dosing.
Using a 25 ml serological pipette, pipette up and down to mix. Pipette 15 ml of the mixture into each small Petri plate.
Let the mussels sit undisturbed for 24 hrs. Note the time and date.
4. 24 hrs after treatment:
After 24 hrs after dosing, remove the treated water and check for mussel mortality.
Dump out the treated water. Rinse with clean hard water 3 times before adding water to each small Petri plate.
Repeat this process for all the Petri plates.
All the Petri dishes must be autoclaved after testing. After being autoclaved, the jars will we washed with water.
5. Calculate the mortality Mortality (%)=100*(Total dead mussels in the treatment-total dead mussels in the blank)/Total mussels treatment Studies with Commercial Compounds Commercial compounds obtained from Sigma-Aldrich were examined at a final concentration of 11.1 µg/ml. The results are shown in Table 1.

TABLE 1

Molluscicidal Effect of Commercial Compounds

| No | Structure | Conc [µg/ml] | 24 hr | 48 hr | 72 hr | 96 hr |
|---|---|---|---|---|---|---|
| SAR-013 | 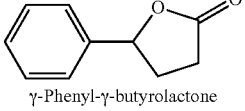 γ-Phenyl-γ-butyrolactone | 11.1 | 0 | 0 | 0 | 0 |
| SAR-011 | 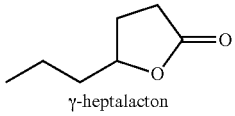 γ-heptalacton | 11.1 | 0 | 0 | 0 | 0 |
| SAR-010 | 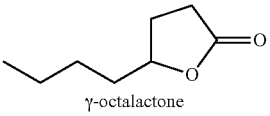 γ-octalactone | 11.1 | 0 | 0 | 0 | 0 |
| SAR-008 | 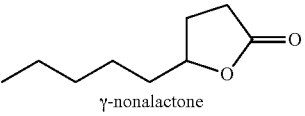 γ-nonalactone | 11.1 | 0 | 0 | 0 | 0 |
| SAR-014 | 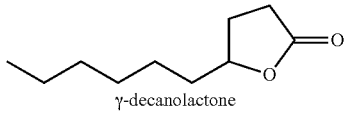 γ-decanolactone | 11.1 | 0 | 0 | 0 | 0 |
| SAR-009 | 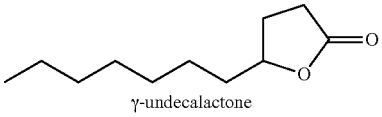 γ-undecalactone | 11.1 | 0 | 0 | 0 | 0 |
| SAR-001 | 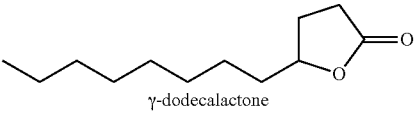 γ-dodecalactone | 11.1 | 86.7 ± 5.8 | 96.7 ± 5.8 | 96.7 ± 5.8 | 96.7 ± 5.8 |
| SAR-006 | 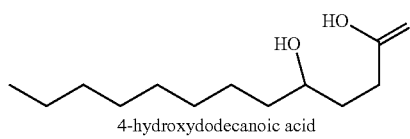 4-hydroxydodecanoic acid | 11.1 | 0 | 0 | 0 | 0 |

TABLE 1-continued

Molluscicidal Effect of Commercial Compounds

| No | Structure | Conc [µg/ml] | 24 hr | 48 hr | 72 hr | 96 hr |
|---|---|---|---|---|---|---|
| SAR-005 | 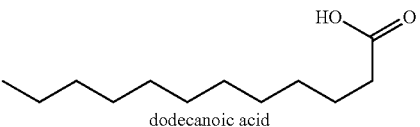 dodecanoic acid | 11.1 | 0 | 0 | 0 | 0 |
| SAR-003 | 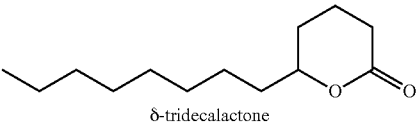 δ-tridecalactone | 11.1 | 3.3 ± 5.7 | 10 ± 10 | 10 ± 10 | 10 ± 10 |
| SAR-004 | 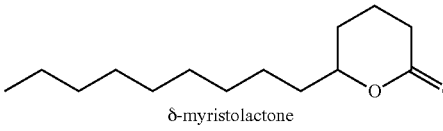 δ-myristolactone | 11.1 | 0 | 0 | 0 | 0 |
| SAR-002 | 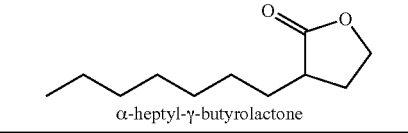 α-heptyl-γ-butyrolactone | 11.1 | 30 ± 10 | 66.7 ± 15.3 | 73.3 ± 11.5 | 76.7 ± 15.3 |

Synthetic Compounds

Synthesized compounds are screened against the *quagga* mussels at a final concentration of 11.1 µg/ml. The following procedure is used to obtain the compounds.

Synthesis of amides: To the ice-cooled carboxylic acid (3 mmole) solution in dichloromethane (20 ml) is sequentially added 1-ethyl-3-(3'-dimethylaminopropyl) carbodiimide (3.3 mmole) and 4-dimethylaminopyridine (3 mmole). After 5 min, amine (3.3 mmole) is added in the reaction solution. The reaction is slowly warmed to the room temperature and lasted overnight. The reaction is extracted with ethyl acetate (200 mL). The organic phase is dried with anhydrous sodium sulfate. After evaporation under vacuum, the residue is run through a silica gel column with an appropriate ratio of ethyl acetate in hexane. The yield of the final products range from 85% to 90%. The final products are characterized with proton NMR.

N-Cyclopentylcinnamamide (SAR-023): 1H NMR (CDCl3): δ (ppm) 7.62 (d, J=15.6 Hz, 1H), 7.50 (d, J=7.0 Hz, 2H), 7.35 (m, 3H), 6.37 (d, J=15.6, 1H), 5.61 (d, J=5.0, Hz, 1H, NH), 4.35 (sextet, J=7.0, 1H), 2.06 (m, 2H), 1.71 (m, 2H), 1.64 (m, 2H), 1.46 (m, 2H).

N-(trans-Cinnamoyl)pyrrolidine (SAR-024): 1H NMR (CDCl3): δ (ppm) 7.70 (d, J=15.5 Hz, 1H), 7.53 (d, J=7.0 Hz, 2H), 7.36 (m, 3H), 6.74 (d, J=15.5, 1H), 3.63 (t, J=7.0, 2H), 3.60 (t, J=7.0, 2H), 2.01 (quintet, J=7.0, 2H), 1.91 (quintet, J=7.0, 2H).

N-(trans-Cinnamoyl)piperidine (SAR-025): 1H NMR (CDCl3): δ (ppm) 7.64 (d, J=15.5 Hz, 1H), 7.52 (d, J=7.2 Hz, 2H), 7.36 (m, 3H), 6.90 (d, J=15.5, 1H), 3.67 (s, 2H), 3.59 (s, 2H), 1.68 (m, 2H), 1.62 (m, 4H).

N-(trans-Cinnamoyl) hexamethleneimine (SAR-026): 1H NMR (CDCl3): δ (ppm) 7.70 (d, J=15.4 Hz, 1H), 7.52 (d, J=7.6 Hz, 2H), 7.36 (m, 3H), 6.88 (d, J=15.4, 1H), 3.63 (t, J=6.0, 2H), 3.61 (t, J=6.0, 2H), 1.76 (m, 4H), 1.59 (m, 4H).

N-Cyclopentyldecanamide (SAR-020): 1H NMR (CDCl3): δ (ppm) 5.35 (br, 1H), 4.22 (sextet, J=7.00, 1H), 2.12 (t, J=7.20, 2H), 1.98 (m, 2H), 1.59-1.67 (m, 6H), 1.26-1.36 (m, 14H), 0.88 (t, J=7.00, 3H).

N-(Decanoyl)pyrrolidine (SAR-007): 1H NMR (CDCl3): δ (ppm) 3.45 (t, J=6.80, 2H), 3.40 (t, J=6.80, 2H), 2.24 (t, J=7.20, 2H), 1.94 (quintet, J=6.80, 2H), 1.84 (quintet, J=6.80, 2H), 1.62 (quintet, J=7.20, 2H), 1.25-1.30 (m, 12H), 0.87 (t, J=7.20, 3H).

N-(Decanoyl)piperidine (SAR-021): 1H NMR (CDCl3): δ (ppm) 3.55 (t, J=5.20, 2H), 3.39 (t, J=5.20, 2H), 2.31 (t, J=7.60, 2H), 1.58-1.65 (m, 4H), 1.52-1.57 (m, 4H), 1.20-1.30 (m, 12H), 0.87 (t, J=7.20, 3H).

N-(Decanoyl)hexamethyleneimine (SAR-022): 1H NMR (CDCl3): δ (ppm) 3.52 (t, J=6.00, 2H), 3.42 (t, J=6.00, 2H), 2.30 (t, J=7.80, 2H), 1.66-1.74 (m, 4H), 1.60-1.66 (m, 2H), 1.50-1.6.0 (m, 4H), 1.20-1.30 (m, 12H), 0.87 (t, J=7.20, 3H).

N-Cyclopentyldecenamide (SAR-027): 1H NMR (CDCl3): δ (ppm) 6.82 (dt, J1=15.20, J2=7.20, 1H), 5.71 (d, J=15.20, 1H), 5.33 (br, 1H), 4.27 (sextet, J=7.00, 1H), 2.15 (m, 2H), 2.10 (m, 2H), 1.67 (m, 2H), 1.60 (m, 2H), 1.40 (m, 4H), 1.28 (m, 8H), 0.88 (t, J=7.00, 3H).

N-(Decenoyl)pyrrolidine (SAR-030): 1H NMR (CDCl3): δ (ppm) 6.90 (dt, J1=15.20, J2=7.00, 1H), 6.07 (d, J=15.20, 1H), 3.52 (t, J=6.30, 2H), 3.50 (t, J=6.30, 2H), 2.19 (m, 2H), 1.96 (quintet, J=7.00, 2H), 1.85 (quintet, J=7.00, 2H), 1.44 (m, 2H), 1.28 (m, 8H), 0.88 (t, J=7.00, 3H).

N-(Decenoyl)piperidine (SAR-031): 1H NMR (CDCl3): δ (ppm) 6.82 (dt, J1=15.20, J2=7.00, 1H), 6.23 (d, J=15.20, 1H), 3.59 (t, J=6.30, 2H), 3.47 (t, J=6.30, 2H), 2.17 (m, 2H), 1.64 (quintet, J=5.60, 2H), 1.56 (quintet, J=5.60, 4H), 1.44 (quintet, J=7.00, 2H), 1.28 (m, 8H), 0.88 (t, J=7.00, 3H).

N-(Decenoyl)hexamethyleneimine (SAR-032): 1H NMR (CDCl3): δ (ppm) 6.91 (dt, J1=15.20, J2=7.00, 1H), 6.21 (d, J=15.20, 1H), 3.57 (t, J=6.00, 2H), 3.49 (t, J=6.00, 2H), 2.17 (m, 2H), 1.73 (m, 4H), 1.56 (m, 4H), 1.45 (m, 2H), 1.28 (m, 8H), 0.88 (t, J=7.00, 3H).

N-(Decenoyl)piperidine (SAR-033): 1H NMR (CDCl3): δ (ppm) 6.82 (dt, J1=15.20, J2=7.00, 1H), 6.23 (d, J=15.20, 1H), 3.59 (t, J=6.30, 2H), 3.47 (t, J=6.30, 2H), 2.17 (m, 2H), 1.64 (quintet, J=5.60, 2H), 1.56 (quintet, J=5.60, 4H), 1.44 (quintet, J=7.00, 2H), 1.28 (m, 8H), 0.88 (t, J=7.00, 3H).

The results are shown in Table 2.

TABLE 2

Potency of synthesized amides toward quagga mussels

| No | Structure | Conc [μg/ml] | 24 hr | 48 hr | 72 hr | 96 hr |
|---|---|---|---|---|---|---|
| SAR-020 | *N-cyclopentyl alkyl amide* | 11.1 | 75 ± 7 | 75 ± 7 | 75 ± 7 | 75 ± 7 |
| SAR-007 | *pyrrolidinyl alkyl amide* | 11.1 | 35 ± 7 | 50 ± 14 | 55 ± 21 | 65 ± 21 |
| SAR-021 | *piperidinyl alkyl amide* | 11.1 | 55 ± 21 | 55 ± 21 | 60 ± 14 | 65 ± 7 |
| SAR-022 | *azepanyl alkyl amide* | 11.1 | 35 ± 7 | 40 ± 14 | 40 ± 14 | 45 ± 21 |
| SAR-023 | *N-cyclopentyl cinnamamide* | 11.1 | 0 | 0 | 0 | 0 |
| SAR-024 | *pyrrolidinyl cinnamamide* | 11.1 | 0 | 0 | 0 | 0 |
| SAR-025 | *piperidinyl cinnamamide* | 11.1 | 0 | 0 | 0 | 0 |
| SAR-026 | *azepanyl cinnamamide* | 11.1 | 0 | 0 | 0 | 0 |
| SAR-027 | *N-cyclopentyl unsaturated alkyl amide* | 11.1 | 85 ± 7 | 95 ± 7 | 95 ± 7 | 95 ± 7 |
| SAR-031 | *pyrrolidinyl unsaturated alkyl amide* | 111 | 20 ± 14 | 35 ± 35 | 35 ± 35 | 40 ± 28 |

TABLE 2-continued

Potency of synthesized amides toward quagga mussels

| No | Structure | Conc [μg/ml] | 24 hr | 48 hr | 72 hr | 96 hr |
|---|---|---|---|---|---|---|
| SAR-032 | 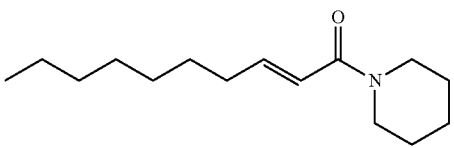 [SMILES: CCCCCCC/C=C/C(=O)N1CCCCC1] | 11.1 | 45 ± 21 | 50 ± 14 | 80 ± 14 | 80 ± 14 |
| SAR-033 | 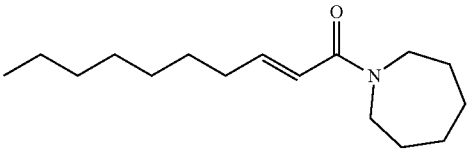 [SMILES: CCCCCCC/C=C/C(=O)N1CCCCCC1] | 11.1 | 70 ± 14 | 75 ± 21 | 75 ± 21 | 75 ± 21 |

Example 2

*Erwinia* Extracts

*Erwinia carotovora* is grown on LB broth (per liter: 10 g tryptone, 5 g yeast extract, 10 g NaCl, pH=7.5). Inoculum is grown by streaking a TSA (tryptic soy agar) plate from a glycerol stock. Purity of the culture is confirmed through visual inspection of colony morphology. Using a sterile 10 μL loop, colonies are collected from the agar surface and resuspended in 50 ml of LB broth in a 250 ml non-baffled Erlenmeyer flask with screw cap. The liquid culture is incubated for 48-72 hours at 200 rpm and 25° C.

After 72 hr, the whole broth is extracted with ethyl acetate. The organic phase is dried under vacuum. The dried extracted is made a 5.0 mg/mL solution in dimethyl sulfoxide (DMSO). Then, such solution (100 μL) is added into 45 mL hard water. The final concentration of ethyl acetate extracts is 11.1 ppm.

Data shown in Table 3 indicates that bioactive compounds against the *quagga* mussels are produced in *Erwinia carotovora* when grown in the LB media. The compound 37 (FIG. 1b) described above is one of the lactones produced by *E. carotovora* grown in the LB media [Gu nter Braden, Solveig Sjoblom, Heidi Hyytia inen, Karen Sims-Huopaniemi, and E. Tapio Palva, *Altering Substrate Chain Length Specificity of an Acylhomoserine Lactone. Synthase in Bacterial Communication, The Journal of Biological Chemistry,* 2005, 280(11) 10403-10409].

TABLE 3

Efficacy of ethyl acetate extracts of *Erwinia carotovora* grown in the LB broth

| Treatments | % mortality (24 hr) | % mortality (48 hr) | % mortality (72 hr) | % mortality (96 hr) | % mortality (120 hr) | % mortality (144 hr) |
|---|---|---|---|---|---|---|
| *Erwinia carotovora* | 30 ± 0 | 75 ± 7 | 80 ± 0 | 80 ± 0 | 80 ± 0 | 90 ± 14 |
| Blank | 0 | 0 | 0 | 0 | 0 | 0 |

Example 3

Isolation of Molluscicidal Compounds from *Pseudomonas*

Study A
Fractionation of Compounds

The following procedure is used for the fractionation of compounds extracted from washed cells of *Pseudomonas fluorescens* CL-145A:

The cell pellet derived from the 10-L fermentation *P. fluorescens* CL 145A (ATCC 55799) in FM2 growth medium is suspended in dilution buffer and extracted with Amberlite XAD-7 resin (Asolkar, R. N., Jensen, P. R., Kauffman, C. A., Fenical, W. 2006. Daryamides A-C, Weakly Cytotoxic Polyketides from a Marine-Derived Actinomycete of the Genus *Streptomyces* strain CNQ-085 *J. Nat. Prod.* 69:1756-1759; Williams, P. G., Miller, E. D., Asolkar, R. N., Jensen, P. R., Fenical, W. 2007. Arenicolides A-C, 26-Membered Ring Macrolides from the Marine Actinomycete *Salinispora arenicola.* J. Org. Chem. 72:5025-5034) by shaking the cell suspension with resin at 225 rpm for two hours at room temperature. The resin and cell mass are collected by filtration through cheesecloth and washed with DI water to remove salts. The resin, cell mass, and cheesecloth are then soaked for 2 h in acetone after which the acetone is filtered and dried under vacuum using rotary evaporator to give the crude extract. The crude extract is then fractionated by using reversed-phase C18 vacuum liquid chromatography ($H_2O$/$CH_3OH$; gradient 90:20 to 0:100%) to give 7 fractions. These fractions are then concentrated to dryness using rotary evaporator and the resulting dry residues are screened for biological activity using both a live mussel jar-test bioassay with *quagga* mussels as well as a cell-based assay with a freshwater snail embryo cell line (*Biomphalaria glabrata*). The bioassays are described in more detail in examples #2 and #3. The active fractions are then subjected to reversed/normal phase HPLC (Spectra System P4000 (Thermo Scientific) to give pure compounds, which are then screened in above mentioned bioassays to locate/identify the active compounds. To confirm the identity of the compound, additional spectroscopic data such as LC/MS and NMR is recorded.

Figure 3:
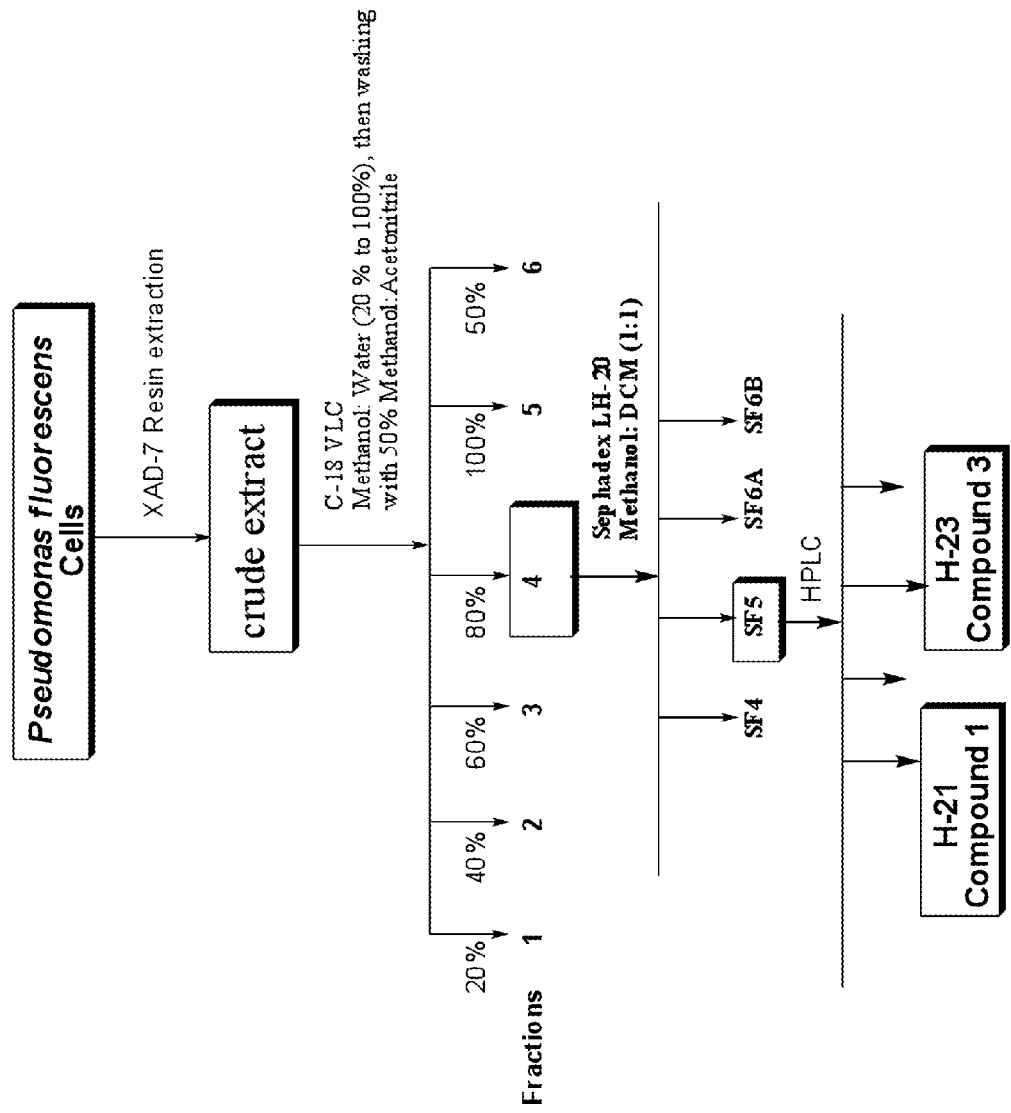
FIG. 3 shows one schematic representation of the purification scheme for obtaining the compounds of the present invention from *Pseudomonas* cell culture.

A diagram of the method used is shown in FIG. 3. Based on both live mussel and snail cell assay, fractions #4 and #5 contain active compounds. Of all compounds separated by HPLC (C-18 column, water: acetonitrile gradient solvent system (0-10 min; 30-40% aqueous $CH_3CN$, 10-20 min; 40-60% aqueous $CH_3CN$, 20-60 min; 60-80% aqueous $CH_3CN$, 60-65 min; 80-100% aqueous $CH_3CN$) at 2.5 mL/min flow rate and UV detection of 210 nm, peaks number 20, retention time 51.66 min, 21, retention time 52.56 min, and 22A retention time 59.61 min inhibits the growth (e.g. low OD600 value) of snail cells in the bioassay.

Mass spectroscopy analysis of active peaks is performed on a Thermo Finnigan LCQ Deca XP Plus electrospray (ESI) instrument using both positive and negative ionization modes in a full scan mode (m/z 100-1500 Da) on a LCQ DECA XP$^{plus}$ Mass Spectrometer (Thermo Electron Corp., San Jose, Calif.). Thermo high performance liquid chromatography (HPLC) instrument equipped with Finnigan Surveyor PDA plus detector, autosampler plus, MS pump and a 4.6 mm×100 mm Luna C18 5 µm column (Phenomenex). The solvent system consists of water (solvent A) and acetonitrile (solvent B). The mobile phase begins at 10% solvent B and is linearly increased to 100% solvent B over 20 min and then kept for 4 min, and finally returned to 10% solvent B over 3 min and kept for 3 min. The flow rate is 0.5 mL/min. The injection volume was 10 µL and the samples are kept at room temperature in an auto sampler. The compounds are analyzed by LC-MS utilizing the LC and reversed phase chromatography. Mass spectroscopy analysis of the present compounds is performed under the following conditions: The flow rate of the nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software. The active compound in peak #20 has a molecular mass of 1294.75 in positive ionization mode. The LC-MS chromatogram for another active compound (peak #22A) suggests a molecular mass of 1320.83 in positive ionization mode.

For structure elucidation, the partially purified compound from active peak #20 is further analyzed using a 600 MHz NMR instrument, and has δ values at δ 9.25, 8.36, 8.06, 7.82, 7.71, 7.52, 7.45, 6.82, 6.36, 6.08, 5.42, 5.39, 5.30, 5.14, 4.68, 4.42, 4.31, 4.16, 4.11, 4.07, 3.95-3.86, 3.83, 3.72, 3.66, 3.53, 3.48, 3.37, 3.17, 3.06, 2.56, 2.53, 2.45, 2.32, 2.21, 2.02, 1.96, 1.84, 1.72, 1.65, 1.61, 1.51, 1.48-1.37, 1.32, 1.12, 0.94, 0.91, 0.68 in CDCl$_3$. The NMR data indicates that the compound contains amino, ester, carboxylic acid, phenyl, indole, aliphatic methyl, ethyl, methylene, oxymethylene, methine, o-methyl, oxymethine and sulfur groups.

Similarly, HPLC analysis on a C-18 column and acetonitrile: water solvent system (0-10 min; 35-45% aqueous CH$_3$CN, 10-20 min; 45-60% aqueous CH$_3$CN, 20-50 min; 60-85% aqueous CH$_3$CN, 50-60 min; 85-100% aqueous CH$_3$CN, 60-70 min; 100% CH$_3$CN) at 10 mL/min flow rate and UV detection of 210 nm of the active fraction #4 using bioassay guided fractionation yielded multiple peaks with activity against both live mussels and snail embryo cells. Most of the activity is concentrated in peaks #27 retention time 47.73 min and #30 retention time 51.52 min.

Peaks #27 and #30 are further analyzed by LC/MS. Based on the results, peak #27 contains multiple compounds with the two main components having a mass of roughly 643 and 984. Peak #30 contains fewer compounds, and the mass analysis suggests a molecular mass around 546 for the main component under the peak.

Mussel Bioassay Test

This live mussel bioassay test is used to guide the identification of active compounds through sample fractionation using HPLC and LC-MS as analytical tools.

Twenty freshly collected *quagga* mussels is placed in a jar containing 250 mL of de-chlorinated tap water at room temperature. Jars are kept at room temperature and connected into a manifold providing constant air supply through bubbling. Each test subject (HPLC fraction or peak) dissolved in DMSO is pipetted into jars separately at a concentration of 1-5 mg, and the mussels are incubated with the test subject for 24 hours. After the incubation period, water in each jar is discarded, and the mussels are rinsed with fresh water and transferred into open glass petri dishes for a 10-day observation period. Mussels are checked daily for mortality, and the dead mussels are removed and discarded. Each treatment is carried out in three replicates, and in the end of the 10-day incubation period, % mortality is calculated for each treatment.

Cell-Based Assay

As an alternative method, this cell-based assay is used as a tool to facilitate the isolation and identification of active compounds in the *P. fluorescens* cells after fermentation. Embryonic cells of a freshwater snail (*Biomphalaria glabrata*, ATCC CRL-1494) are used as a model system for mussel digestive gland epithelial cells known to be susceptible for the *P. fluorescens* biotoxins. For the assay, 200 uL of actively growing cells in a complete growth medium containing *Drosophila* medium, fetal calf serum, d-galactose, and lactalbumin is added into each well of a sterile 96-well plate. The test compound (HPLC fraction or peak at 20 mg/mL) dissolved in DMSO is added into each well, and the plate is covered and incubated in a controlled environment at 23° C. and 5% CO$_2$. Activity (growth inhibition=low turbidity) is measured at 600 nm using a SpectraMax plate reader with the SoftMax Pro software, and compared to the negative control with pure DMSO as a test compound. Each treatment is run in four replicates, and one replicated positive control treatment is included in each plate.

Study B

Methods and Materials

The following procedure is used for the purification of compounds extracted from cell culture of *Pseudomonas fluorescens* and is summarized in FIG. 3. Specifically, the cell pellet derived from the 10-L fermentation *P. fluorescens* CL 145A (ATCC 55799) in FM2 growth medium is suspended in dilution buffer and extracted with Amberlite XAD-7 resin (Asolkar, R. N., Jensen, P. R., Kauffman, C. A., Fenical, W. 2006. Daryamides A-C, Weakly Cytotoxic Polyketides from a Marine-Derived Actinomycete of the Genus *Streptomyces* strain CNQ-085 J. Nat. Prod. 69:1756-1759 and Williams, P. G., Miller, E. D., Asolkar, R. N., Jensen, P. R., Fenical, W. 2007. Arenicolides A-C, 26-Membered Ring Macrolides from the Marine Actinomycete *Salinispora arenicola*. J. Org. Chem. 72:5025-5034) by shaking the cell suspension with resin at 225 rpm for two hours at room temperature. The resin and cell mass are collected by filtration through cheesecloth and washed with DI water to remove salts. The resin, cell mass, and cheesecloth are then soaked for 2 h in acetone after which the acetone is filtered and dried under vacuum using rotary evaporator to give the crude extract. The crude extract is then fractionated by using reversed-phase C18 vacuum liquid chromatography (H$_2$O/CH$_3$OH; gradient 90:20 to 0:100%) to give 7 fractions. These fractions are then concentrated to dryness using rotary evaporator and the resulting dry residues are screened for biological activity using both a live mussel jar-test bioassay with *quagga* mussels as well as a cell-based assay with a freshwater snail embryo cell line (*Biomphalaria glabrata*). The active fractions are then subjected to reversed phase HPLC (Spectra System P4000 (Thermo Scientific) to give pure compounds, which are then screened in above mentioned bioassays to locate/identify the active compounds. To confirm the identity of the compound, additional spectroscopic data such as LC/MS and NMR is recorded.

The active fraction 4 is further subfractionated by using Sephadex LH 20 size exclusion chromatography to give 7 sub fractions. Purification of Pilferolide A and 11-Hydroxy-12-ene-Octadecanoic Acid is performed by using HPLC C-18 column (Phenomenex, Luna 10u C18 (2) 100 A, 250×30), water:acetonitrile gradient solvent system (0-10 min; 50-60% aqueous CH$_3$CN, 10-20 min; 60-75% aqueous CH$_3$CN, 20-45 min; 75-100% aqueous CH$_3$CN, 45-55 min; 100%

CH₃CN, 55-70 min; 100-50% aqueous CH₃CN) at 8 mL/min flow rate and UV detection of 210 nm, the active peaks number 21, retention time 45.59 min, and 23, retention time 48.53 min.

Mass spectroscopy analysis of active peaks is performed on a Thermo Finnigan LCQ Deca XP Plus electrospray (ESI) instrument using both positive and negative ionization modes in a full scan mode (m/z 100-1500 Da) on a LCQ DECA XP$^{plus}$ Mass Spectrometer (Thermo Electron Corp., San Jose, Calif.). Thermo high performance liquid chromatography (HPLC) instrument equipped with Finnigan Surveyor PDA plus detector, autosampler plus, MS pump and a 4.6 mm×100 mm Luna C18 5 μm column (Phenomenex). The solvent system consisted of water (solvent A) and acetonitrile (solvent B). The mobile phase begins at 10% solvent B and is linearly increased to 100% solvent B over 20 min and then kept for 4 min, and finally returned to 10% solvent B over 3 min and kept for 3 min. The flow rate is 0.5 mL/min. The injection volume was 10 μL and the samples are kept at room temperature in an auto sampler. The compounds are analyzed by LC-MS utilizing the LC and reversed phase chromatography. Mass spectroscopy analysis of the present compounds is performed under the following conditions: The flow rate of the nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software. The active compound Piliferolide A has a molecular mass of 295.65 in negative ionization mode. The LC-MS chromatogram for another active compound suggests a molecular mass of 297.74 in negative ionization mode. For structure elucidation, the purified compound Piliferolide A with a molecular weight 296 is further analyzed using a 500 MHz NMR instrument; the reference is set on the internal standard tetramethylsilane (TMS, 0.00 ppm). The compound has ¹H NMR δ values at 5.62, 5.42, 4.55, 3.97, 2.58, 2.35, 2.04, 1.88, 1.73, 1.64, 1.54, 1.39, 0.92 and has ¹³C NMR values of δ 179.1, 133.3, 131.3, 81.9, 72.6, 37.3, 35.4, 32.1, 31.3, 29.5, 29.4, 29.0, 28.6, 27.8, 25.4, 25.3, 22.5, 13.3. The detailed 1D and 2D NMR analysis confirm the structure for the compound as Piliferolide A as a known compound.

The second purified compound with a molecular weight 298 is further analyzed using a 500 MHz NMR instrument, and has ¹H NMR δ values at 5.61, 5.41, 3.96, 2.27, 2.04, 1.69, 1.51, 1.42, 1.32, 0.92 and ¹³C NMR values of δ 176.6, 133.2, 132.6, 73.5, 37.5, 33.9, 32.4, 31.6, 29.8, 29.7, 29.6, 29.4, 29.3, 29.1, 25.7, 24.9, 22.8, 14.3. The detailed 1D and 2D NMR analysis confirm the structure to the compound which is not reported for microbial source; Molecular formula C₁₈H₃₄O₃. The structure of the compound, 11-Hydroxy-12-ene-Octadecanoic Acid is shown below:

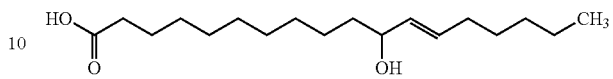

The potency of compounds isolated from *Pseudomonas* cell culture is tested using procedures described above. The results are shown below in Table 4.

TABLE 4

Molluscicidal Effects of Piliferolide A and 11-Hydroxy-12-ene-octadecanoic acid

| Structure | Conc [μg/ml] | % mortality 24 hr | % mortality 48 hr | % mortality 72 hr | % mortality 96 hr |
|---|---|---|---|---|---|
| Piliferolide A | 16 | 53.3 ± 15.3 | 53.3 ± 15.3 | 70 ± 10 | 80 ± 10 |
| 11-Hydroxy-12-ene-octadecanoic acid | 16 | 0 | 20 ± 20 | 33.3 ± 20.8 | 40 ± 26.5 |

Example 5

Kaolin Effects

The effect of kaolin clay on the efficacy of a microbial biopesticide based on *P. fluorescens* bacteria is tested in a biobox study conducted at 11.8° C. On the first day the experiment, kaolin clay is applied to the biobox from a concentrated stock solution via a peristaltic pump so that the final turbidity in the biobox is approximately 20 NTU (normalized turbidity units). Fifty *quagga* mussels are placed in 1-foot long acrylic tubes closed with a nylon mesh at both ends, and the tubes are placed in the bottom of the biobox for the treatment. The duration of the clay application is 6 hours, after which the mussels in the acrylic tubes were exposed to fresh running water in the biobox for 18 hours. The following day, extra clay is cleaned off from bottom the biobox, and the biopesticide in aqueous suspension was applied via a peristaltic pump to a final concentration of 200 ppm. After the 6-hour biopesticide treatment, mussels in tubes are incubated in the biobox with fresh running water at a rate of 1 gallon per minute. Mussels are observed and counted weekly for 5 weeks for determination of % mortality. The control treatments included an untreated control, a treatment with only kaolin clay (with no biopesticide) and a treatment with only biopesticide (with no clay pre-treatment). All treatments are run in three replicates.

Figure 4:
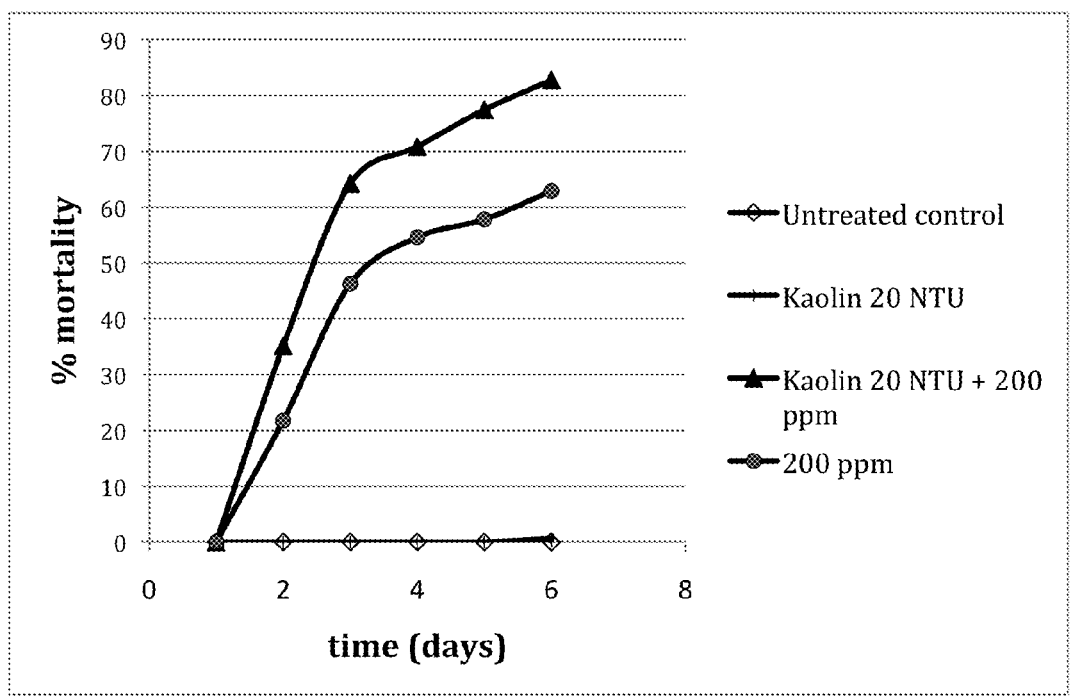
FIG. 4 shows development of mortality over time for mussels treated with clay and *P. fluorescens* biopesticide product in a biobox.

Results presented in Table 5 and FIG. 4 show a significant increase in mortality for mussels exposed to kaolin clay 18 hours before the biopesticide treatment compared with mussels with no clay pre-treatment. This phenomenon can be explained by increased siphoning activity of mussels harvested and treated in cold (11.8° C.) water during the period of low biological activity. This increased siphoning results in greater uptake of pesticide product, which in turn results in increased mussel mortality.

TABLE 5

Efficacy of biopesticide expressed as % mortality measured at each time point (days)

| | % mortality | | | | | |
|---|---|---|---|---|---|---|
| | 1 | 9 | 16 | 21 | 27 | 34 |
| Untreated control | 0 | 0 | 0 | 0 | 0 | 0 |
| Kaolin 20 NTU | 0 | 0 | 0 | 0 | 0 | 1 |
| Kaolin 20 NTU + 200 ppm | 0 | 35 | 64 | 71 | 77 | 83 |
| 200 ppm | 0 | 22 | 46 | 55 | 58 | 63 |

Example 6

Effects of Gamma-Dodecalactone and N-Decenoyl)Pyrrolidine on Snails

Snail Experiments:

An appropriate amount of a testing compound is dissolved in acetone (2 mL) first. The solution was added into 2.5 gram of corn starch and mixed well. The resulting mixture is transferred to a Petri dish (Φ 25 mm). The Petri dish is then put in the hood for natural dry. After drying, water (2 mL) is added into the Petri dish to make paste.

Brown garden snails (*Cantareus aspersus*) are collected from a house garden and raised at least 1 day in lab with cabbage or red carrot. Five individuals with a similar size are chosen for each treatment and transferred into a 1 L beaker. To make the snail active, some water is sprayed on them and in the beaker by using hand-sprayer. After spraying water, the Petri dish with chemical-containing corn starch is placed into the beaker the beaker is covered on the top with aluminum foil. Eating behavior, consumed amount of corn starch and mortality at 24 hr is recorded.

The data indicates (set forth in Table 6) that gamma-dodecalactone (SAR-014) at 100 mg/gram corn starch would strongly repel brown garden snails. However, N-decenoyl) pyrrolidine (SAR-030) in 100 mg/gram corn starch would kill all brown garden snails after they ate.

TABLE 6

Chemical effects on brown garden snail

| treatment | chemical | Dose (mg/gram corn starch) | Eating behavior | Consumed amount of corn starch | 24 hr mortality |
|---|---|---|---|---|---|
| control | | 0 | All individuals ate corn starch | Finishing all corn starch within 2 hr | 0% |
| 1 | SAR-014 | 100 | All individuals quickly escaped from the starch | 0% after 24 hr | 0% |
| 2 | SAR-030 | 100 | Four individuals out of five ate a little bit of starch and walked away. | Less than 5% of corn starched were consumed after 24 hr | All individuals which ate the corn starch were dead |

Although this invention has been described with reference to specific embodiments, the details thereof are not to be construed as limiting, as it is obvious that one can use various equivalents, changes and modifications and still be within the scope of the present invention.

Various references are cited throughout this specification, each of which is incorporated herein by reference in its entirety.

What is claimed is:

1. A method for controlling one or more molluscs comprising:
introducing fatty acid and kaolinite in a body of water or a solid surface of pipes made of iron and/or polyvinyl chloride, in amounts effective for controlling said molluscs.

2. The method according to claim 1, wherein said wherein said fatty acid comprises a hydroxylated unsaturated fatty acid structure comprising at least one carboxylic acid moiety, at least one unsaturated moiety and at least one alcohol group; a molecular weight from 285 to about 310 in the core structure; at least 15 carbons and at least 3 oxygens.

3. The method according to claim 1, wherein said fatty acid comprises 11-hydroxy-12-ene-octadecanoic acid.

4. The method according to claim 1, wherein said fatty acid is derived from a *Pseudomonas fluorescens* or cell suspension from *Pseudomonas fluorescens*.

5. A method for controlling one or more molluscs comprising:
introducing fatty acid and kaolinite in a body of water or a solid surface of pipes made of iron and/or polyvinyl chloride, in amounts effective for controlling said molluscs, wherein said fatty acid for controlling molluscs is present in an amount to result in at least about a 20% mortality of said molluscs relative to untreated control and said kaolinite is present in an amount sufficient to increase mortality rate of said fatty acid for controlling molluscs by at least 20%.

6. The method according to claim 5, wherein said wherein said fatty acid comprises a hydroxylated unsaturated fatty acid structure comprising at least one carboxylic acid moiety, at least one unsaturated moiety and at least one alcohol group; a molecular weight from 285 to about 310 in the core structure; at least 15 carbons and at least 3 oxygens.

7. The method according to claim 5, wherein said fatty acid comprises 11-hydroxy-12-ene-octadecanoic acid.

8. The method according to claim 5, wherein said fatty acid is derived from a *Pseudomonas fluorescens* or cell suspension from *Pseudomonas fluorescens*.

* * * * *